(12) United States Patent
Zhang et al.

(10) Patent No.: US 12,396,699 B2
(45) Date of Patent: Aug. 26, 2025

(54) IMAGING SYSTEMS AND METHODS

(71) Applicant: SHANGHAI UNITED IMAGING HEALTHCARE CO., LTD., Shanghai (CN)

(72) Inventors: Yu Zhang, Shanghai (CN); Jie Niu, Shanghai (CN); Hanyu Wang, Shanghai (CN); Juan Feng, Shanghai (CN); Na Zhang, Shanghai (CN); Le Yang, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 286 days.

(21) Appl. No.: 18/048,420

(22) Filed: Oct. 20, 2022

(65) Prior Publication Data
US 2023/0064456 A1    Mar. 2, 2023

Related U.S. Application Data

(63) Continuation of application No. PCT/CN2021/088540, filed on Apr. 20, 2021.

(30) Foreign Application Priority Data

Apr. 20, 2020   (CN) .......................... 202010310854.5
Jun. 5, 2020    (CN) .......................... 202010505085.4
(Continued)

(51) Int. Cl.
A61B 6/00    (2024.01)

(52) U.S. Cl.
CPC .............. *A61B 6/545* (2013.01); *A61B 6/481* (2013.01); *A61B 6/488* (2013.01); *A61B 6/5241* (2013.01)

(58) Field of Classification Search
CPC ......... A61B 6/545; A61B 6/481; A61B 6/488; A61B 6/5241; A61B 6/482; A61B 6/4417;
(Continued)

(56) References Cited

U.S. PATENT DOCUMENTS 5,208,746 A    5/1993  King et al.
6,018,562 A    1/2000  Willson
(Continued)

FOREIGN PATENT DOCUMENTS

CN    101147684 A    3/2008
CN    102121908 A    7/2011
(Continued)

OTHER PUBLICATIONS

Tang, Guangjian et al., Modern Whole-Body CT Diagnostics, China Medical Science Press, 2008, 17 pages.
(Continued)

*Primary Examiner* — Marcus H Taningco
(74) *Attorney, Agent, or Firm* — METIS IP LLC

(57) ABSTRACT

The present disclosure relates to a method for generating an image. The method may include obtaining a preliminary image of an object. The method may include determining a plurality of point radiation sources of at least one array radiation source at least partially based on an ROI of the object. The method may include determining at least one scanning parameter associated with the plurality of point radiation sources based on the preliminary image. The method may include causing the plurality of point radiation sources to emit radiation beams to the ROI to generate scan data relating to the ROI based on the at least one scanning parameter. The method may include obtaining scan data
(Continued)

relating to the ROI. The method may further include generating a target image of the ROI based on the scan data relating to the ROI.

17 Claims, 13 Drawing Sheets

(30) Foreign Application Priority Data

Jun. 5, 2020 (CN) .......................... 202010509682.4
Aug. 13, 2020 (CN) .......................... 202010813300.4
Sep. 3, 2020 (CN) .......................... 202010916703.7

(58) Field of Classification Search
CPC ......... A61B 6/502; A61B 6/54; A61B 6/4007; H01J 2235/062; H01J 2235/068
See application file for complete search history.

(56) References Cited

U.S. PATENT DOCUMENTS

| | | |
|---|---|---|
| 2002/0045833 A1 | 4/2002 | Wake et al. |
| 2004/0179643 A1 | 9/2004 | Gregerson et al. |
| 2005/0135550 A1 | 6/2005 | Man et al. |
| 2007/0036263 A1 | 2/2007 | Nishide et al. |
| 2007/0280407 A1 | 12/2007 | Kunze et al. |
| 2008/0226024 A1 | 9/2008 | Strommer |
| 2009/0022264 A1 | 1/2009 | Zhou et al. |
| 2010/0008465 A1 | 1/2010 | Matsuura et al. |
| 2010/0097378 A1 | 4/2010 | Barth et al. |
| 2010/0246759 A1 | 9/2010 | Ogura et al. |
| 2012/0051513 A1 | 3/2012 | Nishino et al. |
| 2012/0051522 A1 | 3/2012 | Nishino et al. |
| 2012/0128124 A1 | 5/2012 | Sabol et al. |
| 2013/0044861 A1 | 2/2013 | Muller et al. |
| 2014/0288420 A1 | 9/2014 | Goossen et al. |
| 2015/0131773 A1 | 5/2015 | Lowe et al. |
| 2015/0282774 A1 | 10/2015 | Lee et al. |
| 2016/0106382 A1* | 4/2016 | Lu .......................... A61B 6/4007 600/428 |
| 2016/0183896 A1 | 6/2016 | Muller et al. |
| 2018/0038807 A1 | 2/2018 | Hauser et al. |
| 2018/0165840 A1 | 6/2018 | Bernard et al. |
| 2019/0209107 A1* | 7/2019 | Vogtmeier ............... A61B 6/54 |
| 2020/0211240 A1 | 7/2020 | Bernard |
| 2022/0386969 A1 | 12/2022 | Smith et al. |
| 2023/0008465 A1 | 1/2023 | Smith et al. |

FOREIGN PATENT DOCUMENTS

| | | |
|---|---|---|
| CN | 102551783 A | 7/2012 |
| CN | 103284734 A | 9/2013 |
| CN | 103462630 A | 12/2013 |
| CN | 103700123 A | 4/2014 |
| CN | 104268846 A | 1/2015 |
| CN | 105997127 A | 10/2016 |
| CN | 106408648 A | 2/2017 |
| CN | 106651982 A | 5/2017 |
| CN | 107220933 A | 9/2017 |
| CN | 107811646 A | 3/2018 |
| CN | 109350097 A | 2/2019 |
| CN | 110192885 A | 9/2019 |
| CN | 111265231 A | 6/2020 |
| CN | 111616728 A | 9/2020 |
| CN | 111631742 A | 9/2020 |
| CN | 111956248 A | 11/2020 |
| CN | 111991015 A | 11/2020 |
| DE | 102016207071 A1 | 10/2017 |
| EP | 1005257 A2 | 5/2000 |
| JP | 2012066063 A | 4/2012 |
| WO | 2017194727 A1 | 11/2017 |

OTHER PUBLICATIONS

The Extended European Search Report in European Application No. 21792069.3 mailed on Jul. 24, 2023, 8 pages.
International Search Report in PCT/CN2021/088540 mailed on Jul. 22, 2021, 5 pages.
Written Opinion in PCT/CN2021/088540 mailed on Jul. 22, 2021, 5 pages.

* cited by examiner

1300

1400

IMAGING SYSTEMS AND METHODS

CROSS-REFERENCE TO RELATED APPLICATIONS

This application is a Continuation of International Application No. PCT/CN2021/088540, filed on Apr. 20, 2021, which claims priority to Chinese Patent Application No. 202010310854.5, filed on Apr. 20, 2020, Chinese Patent Application No. 202010505085.4, filed on Jun. 5, 2020, Chinese Patent Application No. 202010509682.4, filed on Jun. 5, 2020, Chinese Patent Application No. 202010916703.4, filed on Sep. 3, 2020, and Chinese Patent Application No. 202010813300.7, filed on Aug. 13, 2020, and the contents of each of which are hereby incorporated by reference.

TECHNICAL FIELD

The present disclosure generally relates to imaging technology, and in particular, to systems and methods for imaging using an array radiation source.

BACKGROUND

Medical imaging techniques, such as an X-ray imaging technique, a computed tomography (CT) imaging technique, or the like, are widely used for disease diagnosis and treatment. Traditional medical imaging techniques may use a radiation source with a hot cathode and may take a relatively long time to scan an object (e.g., a patient). Meanwhile, the object may slightly move voluntarily or involuntarily, and motion artifacts may be generated, thereby affecting the resolution and accuracy of images generated based on the scan. In addition, the traditional medical imaging techniques may be inconvenient to image an object with a relatively complicated structure. Therefore, it is desirable to provide methods and systems to image an object flexibly and conveniently, within a relatively short time.

In some embodiments, the object (e.g., the breast of the patient) may have a compact structure and a relatively large density, a region of interest (ROI) of the object may be shielded by other tissues, and thus, tissues may be overlapped in two-dimensional images generated by scanning the object, and a plurality of artifacts may exit in the images, thereby reducing the resolution and accuracy of the generated images. Therefore, it is desirable to provide methods and systems to generate images with relatively high resolution and improve the imaging quality.

SUMMARY

In one aspect of the present disclosure, a method for generating an image is provided. The method may include obtaining a preliminary image of an object. The method may include determining a plurality of point radiation sources of at least one array radiation source at least partially based on an ROI of the object. The method may include determining at least one scanning parameter associated with the plurality of point radiation sources based on the preliminary image. The method may include causing the plurality of point radiation sources to emit radiation beams to the ROI to generate scan data relating to the ROI based on the at least one scanning parameter. The method may include obtaining scan data relating to the ROI. The method may include generating a target image of the ROI based on the scan data relating to the ROI.

In some embodiments, the preliminary image of the object may include at least one of an X-ray image of the object, an infrared image of the object, a microwave image of the object, an ultrasound image of the object, a nuclear magnetic resonance image of the object, a nuclide image of the object, a visible-light image of the object, or an impedance image of the object.

In some embodiments, each of the plurality of point radiation sources of the at least one array radiation source may include a cold cathode.

In some embodiments, to determine a plurality of point radiation sources of at least one array radiation source, the method may include determining the plurality of point radiation sources from the at least one array radiation source based on at least one first parameter associated with each point radiation source of the at least one array radiation source and at least one second parameter associated with the ROI.

In some embodiments, the at least one first parameter associated with each point radiation source of the at least one array radiation source may include at least one of a source-to-image distance (SID), a source-to-object distance (SOD), a position of the each point radiation source, or a radiation region of the each point radiation source.

In some embodiments, the at least one second parameter associated with the ROI may include at least one of a thickness of the ROI, an attenuation characteristic of the ROI, a shape of the ROI, a position of the ROI, or a size of the ROI. The method may further include determining the at least one second parameter associated with the ROI based on the preliminary image.

In some embodiments, the determining at least one scanning parameter associated with the plurality of point radiation sources may include determining the at least one scanning parameter based on the at least one second parameter.

In some embodiments, the at least one scanning parameter may include at least one of a radiation dose of each of the plurality of point radiation sources, a radiation angle of each of the plurality of point radiation sources, a radiation time of each of the plurality of point radiation sources, a count of the plurality of point radiation sources, or a radiation sequence of the plurality of point radiation sources.

In some embodiments, to determine a plurality of point radiation sources of at least one array radiation source, the method may include determining a plurality of groups of point radiation sources from the at least one array radiation source. Radiation regions of the plurality of groups of point radiation sources may cover the ROI. Radiation regions of each group of point radiation sources may have no overlapping region.

In some embodiments, the causing the plurality of point radiation sources to emit radiation beams to the ROI may include directing the plurality of groups of point radiation sources to emit radiation beams one group after another. Each group of point radiation sources may be directed to synchronously emit radiation beams.

In some embodiments, to cause the plurality of point radiation sources to emit radiation beams to the ROI, the method may include directing the plurality of point radiation sources to emit radiation beams to the ROI in a first mode to generate a first set of data. The method may include directing the plurality of point radiation sources to emit radiation beams to the ROI in a second mode to generate a second set of data.

In some embodiments, the method may include determining a first portion of the scan data by combining the first set of data and determining a second portion of the scan data by combing the second set of data.

In some embodiments, the obtaining scan data relating to the ROI may include obtaining the scan data relating to the ROI by fusing the first portion of the scan data and the second portion of the scan data.

In some embodiments, to generate a target image of the ROI based on the scan data relating to the ROI, the method may include generating a first image based on the first portion of the scan data, generating a second image based on the second portion of the scan data, and generating the target image based on the first image and the second image.

In some embodiments, the first mode may include a mode in which the radiation beams emitted to the ROI have a relatively high energy, and the second mode may include a mode in which the radiation beams emitted to the ROI have a relatively low energy, or the first mode may include a mode in which the object is injected with a contrast agent, and the second mode may include a mode in which the object is injected with no contrast agent.

In some embodiments, the scan data relating to the ROI may include a plurality of pieces of data corresponding to a plurality of sub-regions of the ROI. To generate a target image of the ROI based on the scan data relating to the ROI, the method may include generating a plurality of images corresponding to the plurality of sub-regions of the ROI based on the plurality of pieces of data corresponding to the plurality of sub-regions of the ROI. The method may include generating the target image of the ROI by stitching the plurality of images corresponding to the plurality of sub-regions of the ROI.

In some embodiments, the plurality of sub-regions may include at least one sub-region covered by an overlapping region of radiation regions of two or more point radiation sources of the plurality of point radiation sources.

In some embodiments, to generate the target image of the ROI by stitching the plurality of images corresponding to the plurality of sub-regions of the ROI, the method may include determining a relative position relationship between the plurality of sub-regions of the ROI in the plurality of images. The method may include stitching the plurality of images based on the relative position relationship.

In another aspect of the present disclosure, a system for generating an image is provided. The system may include at least one storage device storing a set of instructions and at least one processor in communication with the storage device. When executing the set of instructions, the at least one processor may be configured to cause the system to obtain a preliminary image of an object. The system may determine a plurality of point radiation sources of at least one array radiation source at least partially based on an ROI of the object. The system may determine at least one scanning parameter associated with the plurality of point radiation sources based on the preliminary image. The system may cause the plurality of point radiation sources to emit radiation beams to the ROI to generate scan data relating to the ROI based on the at least one scanning parameter. The system may obtain scan data relating to the ROI. The system may generate a target image of the ROI based on the scan data relating to the ROI.

In another aspect of the present disclosure, a non-transitory computer readable medium storing instructions is provided. When at least one processor executes the instructions, the instructions may cause the at least one processor to implement a method comprising obtaining a preliminary image of an object. The method may include determining a plurality of point radiation sources of at least one array radiation source at least partially based on an ROI of the object. The method may include determining at least one scanning parameter associated with the plurality of point radiation sources based on the preliminary image. The method may include causing the plurality of point radiation sources to emit radiation beams to the ROI to generate scan data relating to the ROI based on the at least one scanning parameter. The method may include obtaining scan data relating to the ROI. The method may include generating a target image of the ROI based on the scan data relating to the ROI.

In another aspect of the present disclosure, a method for determining a radiation source is provided. The method may include obtaining a preliminary image of an object. The method may include determining an ROI based on the preliminary image. The method may include determining a plurality of point radiation sources of at least one array radiation source at least partially based on the ROI.

In another aspect of the present disclosure, a system for determining a radiation source is provided. The system may include at least one storage device storing a set of instructions and at least one processor in communication with the storage device. When executing the set of instructions, the at least one processor may be configured to cause the system to obtain a preliminary image of an object. The system may determine an ROI based on the preliminary image. The system may determine a plurality of point radiation sources of at least one array radiation source at least partially based on the ROI.

In another aspect of the present disclosure, a method for determining a scanning parameter is provided. The method may include obtaining a preliminary image of an object. The method may include determining at least one parameter associated with an ROI of the object based on the preliminary image. The method may include determining at least one scanning parameter associated with a plurality of point radiation sources of at least one array radiation source based on the at least one parameter associated with the ROI.

In another aspect of the present disclosure, a system for determining a scanning parameter is provided. The system may include at least one storage device storing a set of instructions and at least one processor in communication with the storage device. When executing the set of instructions, the at least one processor may be configured to cause the system to obtain a preliminary image of an object. The system may determine an ROI based on the preliminary image. The system may determine at least one scanning parameter associated with a plurality of point radiation sources of at least one array radiation source based on the at least one parameter associated with the ROI.

In another aspect of the present disclosure, a method for generating an image is provided. The method may include determining a plurality of point radiation sources of at least one array radiation source. The plurality of point radiation sources may include one or more groups of point radiation sources. The method may include causing the one or more groups of point radiation sources to emit radiation beams to an ROI to generate scan data relating to the ROI. The method may include causing a first group among the one or more groups of point radiation sources to synchronously emit radiation beams. The method may include generating a target image based on the scan data.

In another aspect of the present disclosure, a system for generating an image is provided. The system may include at least one storage device storing a set of instructions and at least one processor in communication with the storage device. When executing the set of instructions, the at least one processor may be configured to cause the system to determine a plurality of point radiation sources of at least one array radiation source. The plurality of point radiation sources may include one or more groups of point radiation sources. The system may cause the one or more groups of point radiation sources to emit radiation beams to an ROI to generate scan data relating to the ROI. The system may cause a first group among the one or more groups of point radiation sources to synchronously emit radiation beams. The system may generate a target image based on the scan data.

In another aspect of the present disclosure, a method for generating an image is provided. The method may include obtaining a preliminary image of an object. The method may include determining an ROI of the object based on the preliminary image of the object. The method may include determining a plurality of point radiation sources of at least one array radiation source at least partially based on the ROI. The method may include directing the plurality of point radiation sources to emit radiation beams to the ROI in a first mode to generate a first set of data. The method may include directing the plurality of point radiation sources to emit radiation beams to the ROI in a second mode to generate a second set of data. The method may include obtaining scan data relating to the ROI based on the first set of data and the second set of data. The method may include generating a target image of the ROI based on the scan data.

In another aspect of the present disclosure, a system for generating an image is provided. The system may include at least one storage device storing a set of instructions and at least one processor in communication with the storage device. When executing the set of instructions, the at least one processor may be configured to cause the system to obtain a preliminary image of an object. The system may determine an ROI of the object based on the preliminary image of the object. The system may determine a plurality of point radiation sources of at least one array radiation source at least partially based on the ROI. The system may direct the plurality of point radiation sources to emit radiation beams to the ROI in a first mode to generate a first set of data. The system may direct the plurality of point radiation sources to emit radiation beams to the ROI in a second mode to generate a second set of data. The system may obtain scan data relating to the ROI based on the first set of data and the second set of data. The system may generate a target image of the ROI based on the scan data.

In another aspect of the present disclosure, a method for generating an image is provided. The method may include obtaining preliminary image data of an object. The method may include determining an ROI of the object based on the preliminary image data of the object. The method may include causing a plurality of point radiation sources of at least one array radiation source to emit radiation beams to the ROI to generate a plurality of pieces of data corresponding to a plurality of sub-regions of the ROI. The method may include generating a plurality of images corresponding to the plurality of sub-regions of the ROI based on the plurality of pieces of data. The method may include generating a target image of the ROI by stitching the plurality of images corresponding to the plurality of sub-regions of the ROI.

In another aspect of the present disclosure, a system for generating an image is provided. The system may include at least one storage device storing a set of instructions and at least one processor in communication with the storage device. When executing the set of instructions, the at least one processor may be configured to cause the system to obtain preliminary image data of an object. The system may determine an ROI of the object based on the preliminary image data of the object. The system may cause a plurality of point radiation sources of at least one array radiation source to emit radiation beams to the ROI to generate a plurality of pieces of data corresponding to a plurality of sub-regions of the ROI. The system may generate a plurality of images corresponding to the plurality of sub-regions of the ROI based on the plurality of pieces of data. The system may generate a target image of the ROI by stitching the plurality of images corresponding to the plurality of sub-regions of the ROI.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, sections, or assembly of different levels in ascending order. However, the terms may be displaced by another expression if they achieve the same purpose.

Figure 2:
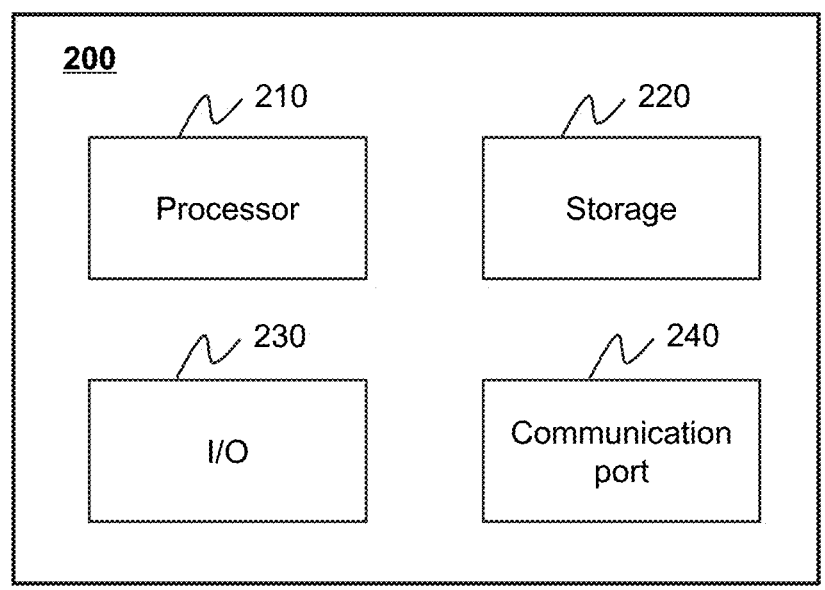
FIG. 2 is a schematic diagram illustrating hardware and/or software components of an exemplary computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., a processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module, or block is referred to as being "on," "connected to," or "coupled to," another unit, engine, module, or block, it may be directly on, connected or coupled to, or communicate with the other unit, engine, module, or block, or an intervening unit, engine, module, or block may be present unless the context clearly indicates otherwise. As used herein, the term "and/or" includes any and all combinations of one or more of the associated listed items. The term "image" in the present disclosure is used to collectively refer to image data (e.g., scan data, projection data) and/or images of various forms, including a two-dimensional (2D) image, a three-dimensional (3D) image, a four-dimensional (4D), one or more image slices, etc. The term "pixel" and "voxel" in the present disclosure are used interchangeably to refer to an element of an image. The term "object" and "subject" in the present disclosure are used interchangeably.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

Provided herein are systems and methods for non-invasive biomedical imaging, such as for disease diagnostic or research purposes. In some embodiments, the systems may include a single modality imaging system and/or a multi-modality imaging system. The single modality imaging system may include, for example, an ultrasound imaging system, an X-ray imaging system, a computed tomography (CT) system, a magnetic resonance imaging (MRI) system, an ultrasonography system, a positron emission tomography (PET) system, an optical coherence tomography (OCT) imaging system, an ultrasound (US) imaging system, an intravascular ultrasound (IVUS) imaging system, a near infrared spectroscopy (NIRS) imaging system, or the like, or any combination thereof. The multi-modality imaging system may include, for example, an X-ray imaging-magnetic resonance imaging (X-ray-MRI) system, a positron emission tomography-X-ray imaging (PET-X-ray) system, a single photon emission computed tomography-magnetic resonance imaging (SPECT-MRI) system, a positron emission tomography-computed tomography (PET-CT) system, a C-arm system, a digital subtraction angiography-magnetic resonance imaging (DSA-MRI) system, etc. It should be noted that the imaging system described below is merely provided for illustration purposes, and not intended to limit the scope of the present disclosure.

The term "imaging modality" or "modality" as used herein broadly refers to an imaging method or technology that gathers, generates, processes, and/or analyzes imaging information of a subject. The subject may include a biological subject and/or a non-biological subject. The biological subject may be a human being, an animal, a plant, or a portion thereof (e.g., a cell, a tissue, an organ, etc.). In some embodiments, the subject may be a man-made composition of organic and/or inorganic matters that are with or without life.

Moreover, the systems and methods disclosed in the present disclosure are described primarily regarding generating a target image in a medical imaging system. It should be understood that this is only one exemplary embodiment. The systems and methods of the present disclosure may be applied to any other kind of system. For example, the systems and methods of the present disclosure may be applied to generate images acquired in different scenarios and/or for different purposes (e.g., safety monitoring, filming, or photography) and/or by different image acquisition devices (e.g., a digital camera, an analog camera, or a scanner).

Generally, an X-ray imaging device may adopt a radiation source with a hot cathode to emit radiation beams to an object to be scanned or treated. The radiation source may be disposed on a gantry of the X-ray imaging device. To scan the object from different angles, the radiation source may be rotated on the gantry. However, the motion (e.g., the rotation) of the radiation source may cause motion artifacts and the thermionic emission mechanism of the hot cathode may cause time delay, thereby reducing the resolution of images generated based on the scan and prolonging the time for scanning the object.

An aspect of the present disclosure relates to systems and methods for generating an image of an object. The systems and methods may obtain a preliminary image of an object. The systems and methods may determine a plurality of point radiation sources of at least one array radiation source at least partially based on a region of interest (ROI) of the object. Each of the plurality of point radiation sources may include a cold cathode and emit radiation beams using a field electron emission mechanism, which may reduce the image artifacts and improve the resolution and quality of the generated images. The at least one array radiation source may have a linear arrangement, a planar arrangement, etc., and may be arranged based on the actual conditions (e.g., the shape and/or size of the scanned object), thereby reducing the radiation dose received by the object and improving the control flexibility of the array radiation source. The systems and methods may determine at least one scanning parameter associated with the plurality of point radiation sources based on the preliminary image. For example, the systems and methods may determine at least one parameter (e.g., second parameter) associated with the ROI (e.g., a thickness of the ROI, an attenuation characteristic of the ROI, a shape of the ROI, a position of the ROI, a size of the ROI, etc.), and determine the scanning parameter based on the at least one parameter associated with the ROI. In some embodiments, the point radiation sources may be controlled to emit radiation beams to the ROI based on the at least one parameter of the ROI, thereby improving the accuracy of the scanning parameter and reducing the radiation dose received by the object. The systems and methods may cause the plurality of point radiation sources to emit (based on the at least one scanning parameter) radiation beams to the ROI to generate scan data relating to the ROI. In some embodiments, the systems and methods may cause the plurality of point radiation sources to emit radiation beams in different manners according to different scanning conditions. For example, the systems and methods may cause two or more groups of the plurality of point radiation sources to synchronously emit radiation beams. As another example, the systems and methods may cause a group among one or more groups of point radiation sources to synchronously emit radiation beams. As a further example, the systems and methods may cause the plurality of point radiation sources to emit radiation beams under one or more modes (e.g., a high energy mode, a low energy mode, a mode in which the object is injected with a contrast agent, a mode in which the object is injected with no the contrast agent, etc.). According to the systems and methods of the present disclosure, the scan time may be efficiently reduced and imaging accuracy may be improved. The systems and methods may further obtain scan data relating to the ROI and/or generate a target image of the ROI based on the scan data. In some embodiments, the systems and methods may generate the target image of the ROI by stitching a plurality of images corresponding to a plurality of sub-regions of the ROI (e.g., based on a relative position relationship between the plurality of sub-regions).

Figure 1:
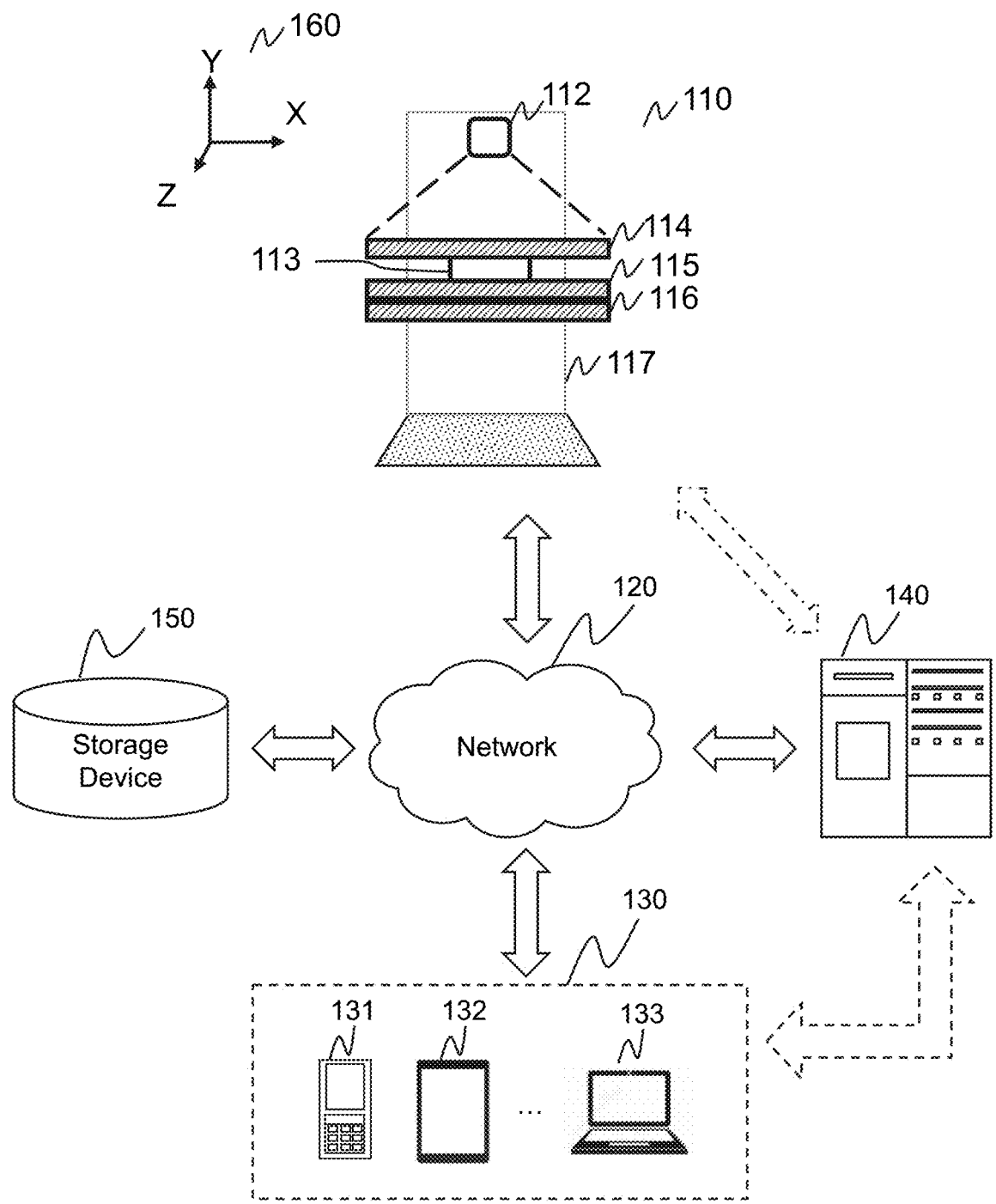
FIG. 1 is a schematic diagram illustrating an exemplary imaging system according to some embodiments of the present disclosure.

FIG. 1 is a schematic diagram illustrating an exemplary imaging system 100 according to some embodiments of the present disclosure.

As illustrated in FIG. 1, the imaging system 100 may include an imaging device 110, a network 120, a terminal 130, a processing device 140, and a storage device 150. The components in the imaging system 100 may be connected in one or more of various ways. Merely by way of example, the imaging device 110 may be connected to the processing device 140 through the network 120. As another example, the imaging device 110 may be connected to the processing device 140 directly as indicated by the bi-directional arrow in dotted lines linking the imaging device 110 and the processing device 140. As yet another example, the storage device 150 may be connected to the processing device 140 directly or through the network 120. As yet another example, the terminal 130 may be connected to the processing device 140 directly (as indicated by the bi-directional arrow in dotted lines linking the terminal 130 and the processing device 140) or through the network 120.

The imaging device 110 may generate or provide image data related to an object 113 via scanning the object 113. In some embodiments, the object 113 may include a biological subject and/or a non-biological object. For example, the object may include a specific portion of a body, such as a head, a thorax, an abdomen, a breast, or the like, or a combination thereof. In some embodiments, the image data relating to the object 113 may include projection data, one or more image slices, one or more 2D images of the subject, one or more 3D images, one or more 4D images of the object, etc. The projection data may include raw data generated by the imaging device 110 by scanning the subject and/or data generated by performing a projection on an image of the subject.

In some embodiments, the imaging device 110 may include a single modality imaging device. For example, the imaging device 110 may include a digital breast tomosynthesis (DBT) device, a full field digital mammography machine (FFDM), a computed tomography (CT) device, a cone beam computed tomography (CBCT) device, a digital subtraction angiography (DSA), a positron emission tomography (PET) device, a single-photon emission computed tomography (SPECT) device, a magnetic resonance imaging (MRI) device (also referred to as an MR device, an MR scanner), an ultrasonography scanner, a digital radiography (DR) scanner, or the like, or any combination thereof. In some embodiments, the imaging device 110 may include a multi-modality imaging device. Exemplary multi-modality imaging devices may include a PET-CT device, a PET-MR device, or the like, or a combination thereof.

Merely by way of example, the imaging device 110 may be a DBT device. The DBT device may include a radiation source 112, a compression component 114, a holder 115, a detector 116, and a gantry 117. The gantry 117 may be configured to support one or more components (e.g., the radiation source 112, the compression component 114, the holder 115, or the detector 116) of the imaging device 110. In some embodiments, the imaging device 110 may include a collimator. The collimator (not shown in the figure) may be configured to control a radiation region (e.g., a radiation field) on the object 113.

In some embodiments, the radiation source 112 may include a hot cathode emission radiation source, a cold cathode emission radiation source, a field emission radiation source, or the like, or any combination thereof. For example, the radiation source 112 may include a cold cathode emission radiation source. As another example, the radiation source 112 may include a field emission radiation source. A field emission radiation source may generate electrons without heating. Specifically, free electrons of a metal of the field emission radiation source may escape from a surface of the metal due to the quantum effect of barrier penetration under an intense electric field. A plurality of materials (e.g., metals (such as a needle tip made of metal), carbon nanotubes, etc.) may emit electrons at room temperature due to the field electron emission mechanism, and obtain an electron beam current. By using the field electron emission mechanism, the startup/shutdown speed of the imaging device 110 may be improved, the imaging device 110 may be more energy-efficient, and no heat dissipation is required.

If the radiation source 112 is the hot cathode emission radiation source, the radiation source 112 may include a voltage generator (not shown in FIG. 1), a tube (not shown in FIG. 1), and the collimator. The voltage generator may be configured to generate a voltage for the tube. The tube may be configured to generate and/or emit a radiation beam based on the voltage. The radiation beam may include a particle ray, a photon ray, or the like, or a combination thereof. In some embodiments, the radiation beam may include a plurality of radiation particles (e.g., neutrons, protons, electron, μ-mesons, heavy ions), a plurality of radiation photons (e.g., X-ray, a γ-ray, ultraviolet, laser), or the like, or a combination thereof.

In some embodiments, for a single field emission radiation source (e.g., a point radiation source), a radiation region of the field emission radiation source may cover only a portion of a region (e.g., an ROI) of the object to be scanned. Thus, in some embodiments, the radiation source 112 may include at least one array radiation source. The at least one array radiation source may have a planar arrangement, a linear arrangement, etc. In some embodiments, the arrangement of the radiation source 112 may be determined based on the actual condition (e.g., a position of the region of the object 113, a shape of the region of the object 113, a size of the region of the object, etc.). In some embodiments, the array radiation source 112 may include a plurality of point radiation sources. The plurality of point radiation sources may be configured to emit radiation beams to the object 113. In this case, a scan time for scanning the object may be significantly reduced, the motion of the imaging device 110 or the object 113 may be reduced, thereby reducing the artifact (e.g., the motion artifact) generated in an image (e.g., a target image) of the object 113 and improving the image quality. In some embodiments, one or more (e.g., each) of the point radiation sources may be a field emission radiation source. More descriptions regarding the point radiation sources may be found elsewhere in the present disclosure. See, e.g., FIG. 7, FIG. 9, and FIG. 12.

The holder 115 and the compression component 114 may be configured to position the object 113 (e.g., a breast). In some embodiments, the holder 115 and/or the compression component 114 may be fixedly or movably attached to the gantry 117. The holder 115 may be placed above the detector 116. The object 113 may be placed on the holder 115. For example, a patient may place her breast on the holder 115. The compression component 114 may be located between the radiation source 112 and the holder 115. For reasons related both to the immobilizing of the object 113 (e.g., the breast) and to image quality or intensity of X-rays delivered to the object 113 (e.g., the breast), by compressing the object 113 (e.g., the breast) during a scan of the object 113, the object 113 may be immobilized during the scan, and the intensity of X-rays delivered to the object 113 may be increased due to the reduced volume of the object 113, thereby improving the quality of an image of the object 113. The compression force may be applied through the compression component 114 that compresses the object 113 (e.g., the breast) on the holder 115. After the breast is compressed by the compression component 114, the shape of the compressed breast may be relatively thin and uniform and soft tissues in the compressed breast may be separated, which may further improve the quality of the images of the breast. In some embodiments, the compression component 114 and the holder 115 may not block the radiation beams emitted by the radiation source 112.

The detector 116 may be configured to detect at least part of the radiation beams. For example, the detector 116 may detect radiation beams emitted by the plurality of point radiation source of the radiation source 112, and generate scan data. In some embodiments, the detector 116 may be disposed opposite to the radiation source 112. In some embodiments, the detector 16 may include a plurality of detecting units. The plurality of detecting units of the 116 may be arranged in any suitable manner, for example, a single row, two rows, or any number of rows. The detector 116 may include a scintillation detector (e.g., a cesium iodide detector), a gas detector, a flat panel detector, or the like. In some embodiments, the detector 116 may include a photon counting detector. The photon counting detector may detect the energy of a detected X-ray photon and the count of the detected X-ray photons. For example, a photomultiplier tube configured on the detector 116 (e.g., the photon counting detector) may be configured to count the detected X-ray photons of different energy ranges.

In some embodiments, the radiation source 112 may rotate around a rotation axis during a scan such that the object 113 is scanned (imaged and/or treated) from a plurality of directions. Merely by way of example, the radiation source 112 may be fixedly or movably attached to the gantry 117, and the detector 116 may be fixedly or flexibly attached to the gantry 117 opposite to the radiation source 112. As used herein, a fixed attachment of component A (e.g., the radiation source 112) to component B (e.g., the gantry 117) indicates that the component A does not move relative to the component B when the component A and the component B are properly assembled and used as intended. As used herein, a moveable attachment of component A (e.g., the radiation source 112) to component B (e.g., the gantry 117) indicates that the component A can move relative to the component B when the component A and the component B are properly assembled and used as intended. When the gantry 117 rotates about a gantry rotation axis, the radiation source 112 and the detector 116 attached on the gantry 117 may rotate along with the gantry 117, and the object 113 may be scanned from a plurality of gantry angles. The gantry rotation axis of the gantry 117 may be in a direction of the Z-axis as illustrated in FIG. 1. As used herein, a gantry angle relates to a position of the radiation source 112 with reference to the medical device 110. For example, a gantry angle may be an angle between a vertical direction and a direction of a beam axis of a radiation beam emitted from the radiation source 112 of the medical device 110. In some embodiments, a driving device (e.g., a motor, a hydraulic cylinder) may be connected to the gantry 117 to drive the gantry 117 to move (e.g., rotate, translate).

Alternatively, one or more point radiation sources of the plurality of point radiation sources of the radiation source 112 may be rotated or moved relative to the object 113. In this case, at least one parameter (e.g., first parameter) (e.g., a radiation region, a position, a radiation angle, etc.) associated with the point radiation source(s) may be adjusted based on the actual conditions (e.g., the size of the object 113, the position of the object 113, the shape of the object 113, etc.).

During the scan of the object 113 (e.g., the breast), radiation beams emitted by the radiation source 112 may traverse the object 113 (e.g., the breast). The detector 116 located opposite to the radiation source 112 may detect at least a portion of the radiation beams that have traversed the object 113 (e.g., the breast). The detector 116 may transform optical signals of the detected radiation beams into digital signals, and transmit the digital signals to the processing device 140 for further processing (e.g., generating a breast image).

In some embodiments, the radiation source 112, the compression component 114, the holder 115, and/or the detector 116 may move along a guide rail to adjust a distance between the radiation source 112 and the detector 116. Alternatively, the radiation source 112 and/or the detector 116 may be rotated or moved relative to the compression component 114 and the holder 115 such that the object 113 is scanned (imaged and/or treated) from a plurality of directions.

The network 120 may facilitate the exchange of information and/or data. In some embodiments, one or more components of the imaging system 100 (e.g., the imaging device 110, the terminal 130, the processing device 140, or the storage device 150) may send information and/or data to other components of the imaging system 100 via the network 120. For example, the processing device 140 may obtain, via the network 120, image data (e.g., 2D images, 3D images, projection data, slice images, etc.) from the storage device 150. In some embodiments, the network 120 may be any type of wired or wireless network, or combination thereof. The network 120 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 120 may include a cable network, a wireline network, an optical fiber network, a telecommunications network, an intranet, an Internet, a local area network (LAN), a wide area network (WAN), a wireless local area network (WLAN), a metropolitan area network (MAN), a wide area network (WAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired or wireless network access points such as base stations and/or internet exchange points through which one or more components of the imaging system 100 may be connected to the network 120 to exchange data and/or information.

The terminal 130 may include a mobile device 131, a tablet computer 132, a laptop computer 133, or the like, or any combination thereof. In some embodiments, the mobile device 131 may include a smart home device, a wearable device, a smart mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, footgear, eyeglasses, a helmet, a watch, clothing, a backpack, an accessory, or the like, or any combination thereof. In some embodiments, the smart mobile device may include a smartphone, a personal digital assistant (PDA), a gaming device, a navigation device, a point of sale (POS) device, or the like, or any combination thereof. In some embodiments, the virtual reality device and/or the augmented reality device may include a virtual reality helmet, a virtual reality glass, a virtual reality patch, an augmented reality helmet, an augmented reality glass, an augmented reality patch, or the like, or any combination thereof. For example, the virtual reality device and/or the augmented reality device may include a Google Glass™, an Oculus Rift™, a HoloLens™, a Gear VR™, etc. In some embodiments, the terminal 130 may remotely operate the imaging device 110. In some embodiments, the terminal 130 may operate the imaging device 110 via a wireless connection. In some embodiments, the terminal 130 may receive information and/or instructions inputted by a user, and send the received information and/or instructions to the imaging device 110 or the processing device 140 via the network 120. In some embodiments, the terminal 130 may receive data and/or information from the processing device 140. In some embodiments, the terminal 130 may be omitted or be part of the processing device 140.

In some embodiments, the processing device 140 may be configured to process data obtained from the imaging device 110, the terminal 130, or the storage device 150. For example, the processing device 140 may process an image (e.g., a preliminary image) of the object 113 obtained from the imaging device 110 or the storage device 150 to determine an ROI of the object 113. As another example, the processing device 140 may obtain the at least one parameter (e.g., the at least one first parameter) associated with each point radiation source of the at least one array radiation source and determine radiation regions of each point radiation source. As yet another example, the processing device 140 may process scan data relating to the ROI obtained from the imaging device 110 or the storage device 150 to generate an image (e.g., a target image) of the ROI. As yet another example, the processing device 140 may obtain the information (e.g., an age, a historical medical record, a body type (e.g., fat or thin)) associated with the object 113 from the storage device 150.

In some embodiments, the processing device 140 may be configured to control the operation of the radiation source 112. For example, the processing device 140 may determine, at least partially based on the ROI of the object, positions of the plurality of point radiation sources (in the radiation source 112) that need to emit radiation beams. As another example, the processing device 140 may control the number or count of point radiation sources (in the radiation source 112) that need to emit radiation beams. As yet another example, the processing device 140 may determine a radiation sequence of the plurality of point radiation sources in the radiation source 112 to emit radiation beams. As yet another example, the processing device 140 may determine the at least one parameter associated with the radiation source 112.

In some embodiments, the processing device 140 may control the operation of the radiation source 112 based on prescribed information relating to radiation. For example, the processing device 140 may determine radiation doses of the plurality of point radiation sources according to the imaging requirements (e.g., an image resolution, an imaging angle, a radiation dose, etc.).

In some embodiments, the processing device 140 may be a single server or a server group. The server group may be centralized or distributed. For example, the processing device 140 may be a central processing unit (CPU), a digital signal processor (DSP), a system on a chip (SoC), a microcontroller unit (MCU), or the like, or any combination thereof. In some embodiments, the processing device 140 may be local or remote. For example, the processing device 140 may access information and/or data stored in the imaging device 110, the terminal 130, and/or the storage device 150 via the network 120. As another example, the processing device 140 may be directly connected to the imaging device 110, the terminal 130, and/or the storage device 150, to access stored information and/or data. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 140 may be implemented on a computing device 200 having one or more components illustrated in FIG. 2 in the present disclosure.

The storage device 150 may store data and/or instructions. In some embodiments, the storage device 150 may store data obtained from the terminal 130 and/or the processing device 140. For example, the storage device 150 may store one or more images obtained from the processing device 140 and/or the imaging device 110. As another example, the storage device 150 may store the scan data obtained from the processing device 140 and/or the imaging device 110. In some embodiments, the storage device 150 may store data and/or instructions that the processing device 140 may execute or use to perform exemplary methods described in the present disclosure. For example, the storage device 150 may store data and/or instructions that the processing device 140 may execute or use to generate an image. In some embodiments, the storage device 150 may include a mass storage device, a removable storage device, a volatile read-and-write memory, a read-only memory (ROM), or the like, or any combination thereof. Exemplary mass storage devices may include a magnetic disk, an optical disk, a solid-state drive, etc. Exemplary removable storage devices may include a flash drive, a floppy disk, an optical disk, a memory card, a zip disk, a magnetic tape, etc. Exemplary volatile read-and-write memory may include a random-access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more components of the imaging system 100 (e.g., the terminal 130, the processing device 140). One or more components of the imaging system 100 may access the data or instructions stored in the storage device 150 via the network 120. In some embodiments, the storage device 150 may be directly connected to or communicate with one or more components of the imaging system 100 (e.g., the terminal 130, the processing device 140). In some embodiments, the storage device 150 may be part of the processing device 140.

In some embodiments, a coordinate system 160 may be provided for the imaging system 100 to define a position of a component and/or the subject (e.g., an absolute position, a position relative to another component). For illustration purposes, the coordinate system 160 may include the X-axis, the Y-axis, and the Z-axis. The X-axis and the Z-axis shown in FIG. 1 may be horizontal, and the Y-axis may be vertical. As illustrated, a positive Z direction along the Z-axis may be from the front side to the back side of the medical device 110 seen from the direction facing the front of the medical device 110; a positive Y direction along the Y-axis shown in FIG. 1 may be from the lower part to the upper part of the medical device 110 (or from the floor to the ceiling of the room where the medical device 110 is located); and the X-axis shown in FIG. 1 may be perpendicular to the Z-axis and the Y-axis.

It should be noted that the above description of the imaging system 100 is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, the radiation source 112 and the detector 116 may be disposed on a ring component of the imaging device 110, a plane component of the imaging device 110, a curved planar component of the imaging device 110, etc. In some embodiments, the imaging system 100 may include one or more additional components. For example, the imaging device 110 may include one or more controllers configured to control the operation of the plurality of point radiation sources. As another example, the one or more controllers and the processing device 140 may be integrated into an independent component to perform the functions of the one or more controllers and the processing device 140. Additionally or alternatively, one or more components of the imaging system 100 described above may be omitted. As another example, two or more components of the imaging system 100 may be integrated into a single component.

FIG. 2 is a schematic diagram illustrating hardware and/or software components of an exemplary computing device according to some embodiments of the present disclosure. The computing device 200 may be used to implement any component of the imaging system 100 as described herein. For example, the processing device 140 and/or the terminal 130 may be implemented on the computing device 200, respectively, via its hardware, software program, firmware, or a combination thereof. Although only one such computing device is shown, for convenience, the computer functions relating to the imaging system 100 as described herein may be implemented in a distributed fashion on a number of similar platforms, to distribute the processing load.

As illustrated in FIG. 2, the computing device 200 may include a processor 210, a storage device 220, an input/output (I/O) 230, and a communication port 240. The processor 210 may execute computer instructions (program code) and, when executing the instructions, cause the processing device 140 to perform functions of the processing device 140 in accordance with techniques described herein. The computer instructions may include, for example, routines, programs, objects, components, signals, data structures, procedures, modules, and functions, which perform particular functions described herein.

In some embodiments, the processor 210 may process data and/or images obtained from the imaging device 110, the terminal 130, the storage device 150, and/or any other component of the imaging system 100. For example, the processor 210 may obtain a preliminary image of an object and/or determine an ROI of the object based on the preliminary image. As another example, the processor 210 may obtain scan data relating to the ROI by scanning the ROI of the object and/or generate a target image based on the scan data relating to the ROI.

In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors. Thus operations and/or method steps that are performed by one processor as described in the present disclosure may also be jointly or separately performed by the multiple processors. For example, if in the present disclosure the processor of the computing device 200 executes both operation A and operation B, it should be understood that operation A and operation B may also be performed by two or more different processors jointly or separately in the computing device 200 (e.g., a first processor executes process A and a second processor executes process B, or the first and second processors jointly execute operations A and B).

The storage device 220 may store data/information obtained from the imaging device 110, the terminal 130, the storage device 150, or any other component of the imaging system 100. In some embodiments, the storage device 220 may include a mass storage device, a removable storage device, a volatile read-and-write memory, a read-only memory (ROM), or the like, or any combination thereof. In some embodiments, the storage device 220 may store one or more programs and/or instructions to perform exemplary methods described in the present disclosure.

The I/O 230 may input or output signals, data, and/or information. In some embodiments, the I/O 230 may enable user interaction with the processing device 140. In some embodiments, the I/O 230 may include an input device and an output device. Exemplary input devices may include a keyboard, a mouse, a touch screen, a microphone, or the like, or a combination thereof. Exemplary output devices may include a display device, a loudspeaker, a printer, a projector, or the like, or a combination thereof. Exemplary display devices may include a liquid crystal display (LCD), a light-emitting diode (LED)-based display, a flat panel display, a curved screen, a television device, a cathode ray tube (CRT), or the like, or a combination thereof.

The communication port 240 may be connected to a network (e.g., the network 120) to facilitate data communications. The communication port 240 may establish connections between the processing device 140 and the imaging device 110, the terminal 130, or the storage device 150. The connection may be a wired connection, a wireless connection, or a combination of both that enables data transmission and reception. The wired connection may include an electrical cable, an optical cable, a telephone wire, or the like, or any combination thereof. The wireless connection may include Bluetooth, Wi-Fi, WiMAX, WLAN, ZIGBEE, mobile network (e.g., 3G, 4G, 5G, etc.), or the like, or a combination thereof. In some embodiments, the communication port 240 may be a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
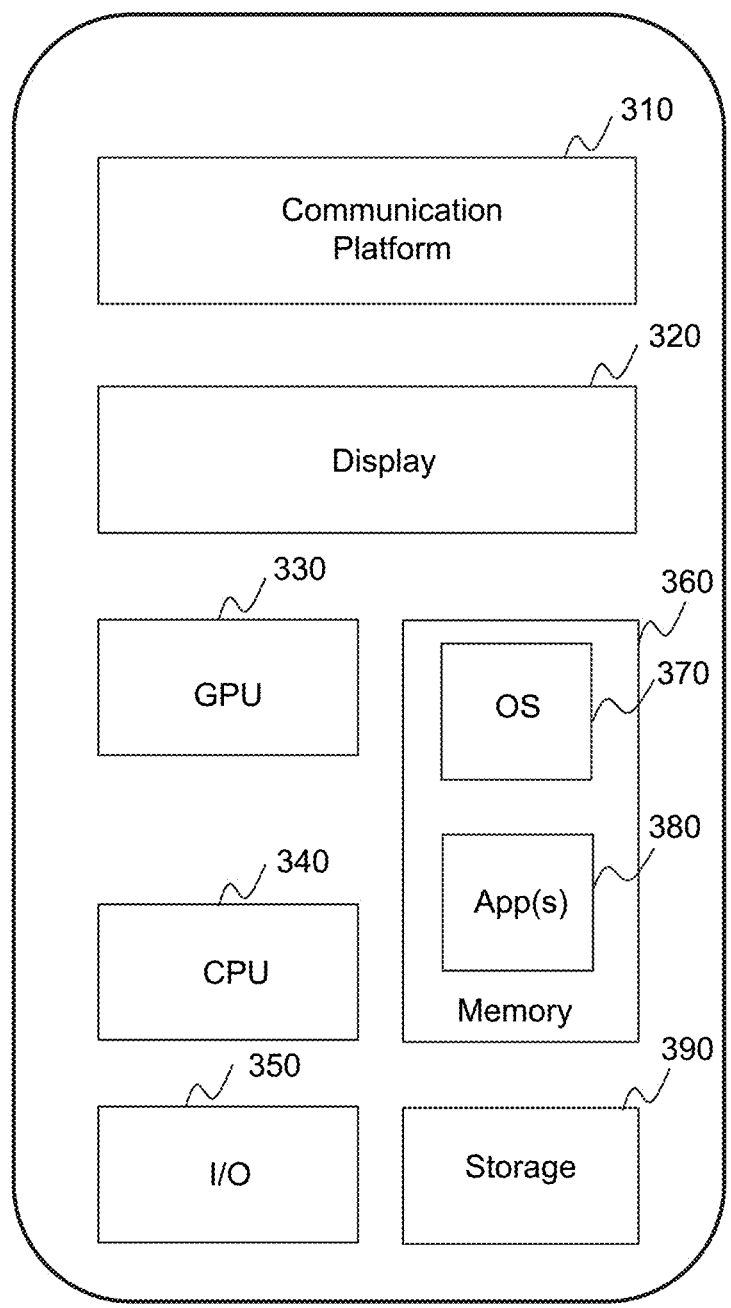
FIG. 3 is a schematic diagram illustrating hardware and/or software components of an exemplary mobile device according to some embodiments of the present disclosure.

FIG. 3 is a schematic diagram illustrating hardware and/or software components of an exemplary mobile device according to some embodiments of the present disclosure. In some embodiments, the processing device 140 and/or the terminal 130 may be implemented on the mobile device 300. As illustrated in FIG. 3, the mobile device 300 may include a communication platform 310, a display 320, a graphics processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS, Android, Windows Phone, etc.) and one or more applications 380 may be loaded into the memory 360 from the storage 390 in order to be executed by the CPU 340. The applications 380 may include a browser or any other suitable mobile apps for receiving and rendering information relating to the imaging system 100 from the processing device 140. User interactions with the information stream may be achieved via the I/O 350 and provided to the processing device 140 and/or other components of the imaging system 100 via the network 120.

To implement various modules, units, and their functionalities described in the present disclosure, computer hardware platforms may be used as the hardware platform(s) for one or more of the elements described herein. The hardware elements, operating systems, and programming languages of such computers are conventional in nature, and it is presumed that those skilled in the art are adequately familiar therewith to adapt those technologies to generate a high-quality image of a subject as described herein. A computer with user interface elements may be used to implement a personal computer (PC) or another type of workstation or terminal device, although a computer may also act as a server if appropriately programmed. It is believed that those skilled in the art are familiar with the structure, programming, and general operation of such computer equipment and as a result, the drawings should be self-explanatory.

Figure 4:
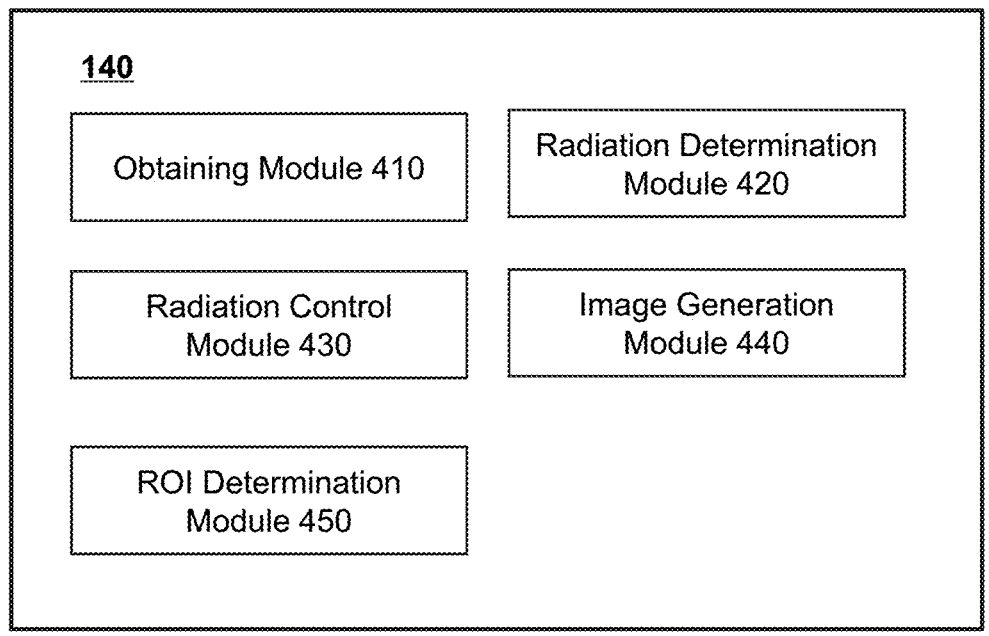
FIG. 4 is a block diagram illustrating an exemplary processing device according to some embodiments of the present disclosure.

FIG. 4 is a block diagram illustrating an exemplary processing device according to some embodiments of the present disclosure. The processing device 140 may include an obtaining module 410, a radiation determination module 420, a radiation control module 430, an image generation module 440, and an ROI determination module 450.

The obtaining module 410 may be configured to obtain information associated with an object. For example, the obtaining module 410 may obtain image data (e.g., a preliminary image, preliminary image data, etc.) of an object. As another example, the obtaining module 410 may obtain scan data relating to an ROI of the object. In some embodiments, the obtaining module 410 may obtain the information associated with an object from one or more components (e.g., the imaging device 110, the storage device 150, the storage device 220, the storage 390, or an external source) of the imaging system 100.

In some embodiments, the radiation determination module 420 may be configured to determine a plurality of point radiation sources of at least one array radiation source at least partially based on the ROI of the object. For example, the 420 may determine at least one first parameter associated with each point radiation source of at least one array radiation source and at least one second parameter associated with an ROI, and determine the plurality of point radiation sources based on at least one first parameter associated with each point radiation source of the at least one array radiation source and at least one second parameter associated with the ROI. In some embodiments, the radiation determination module 420 may determine at least one scanning parameter associated with the plurality of point radiation sources based on the preliminary image.

In some embodiments, the radiation control module 430 may be configured to cause the plurality of point radiation sources to emit radiation beams to the ROI to generate scan data relating to the ROI based on the at least one scanning parameter. In some embodiments, the radiation control module 430 may cause one or more groups of the plurality of point radiation sources to emit radiation beams. For example, the radiation control module 430 may cause a first group among the one or more groups of point radiation sources to synchronously emit radiation beams. As another example, the radiation control module 430 may cause a second group among the one or more groups of the plurality of point radiation sources to synchronously emit radiation beams to the ROI. Radiations of the first group of point radiation sources and the second group of point radiation sources may be performed sequentially. In some embodiments, the radiation control module 430 may direct the plurality of point radiation sources to emit radiation beams to the ROI in different modes (e.g., a high energy mode, a low energy mode, a mode in which the object is injected with a contrast agent, a mode in which the object is not injected with the contrast agent, etc.). In some embodiments, the radiation control module 430 may cause the plurality of point radiation sources of the at least one array radiation source to emit radiation beams to the ROI to generate a plurality of pieces of data corresponding to a plurality of sub-regions of the ROI.

The image generation module 440 may be configured to generate a target image of the ROI based on the scan data relating to the ROI. For example, the image generation module 440 may generate a plurality of images corresponding to the plurality of sub-regions of the ROI based on the plurality of pieces of data. The image generation module 440 may generate the target image of the ROI by stitching the plurality of images corresponding to the plurality of sub-regions of the ROI.

The ROI determination module 450 may be configured to determine the ROI of the object. For example, the ROI determination module 450 may determine the ROI of the object in the preliminary image using an image recognition algorithm. As another example, the ROI determination module 450 may determine a region including the object and a region excluding the object in the preliminary image, and designate the region including the object as the ROI. As yet another example, the ROI determination module 450 may recognize a target region of the object and designate the target region as the ROI.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, the radiation determination module 420 and the ROI determination module 450 may be integrated into a determination module to perform functions of the radiation determination module 420 and the ROI determination module 450.

Figure 5:
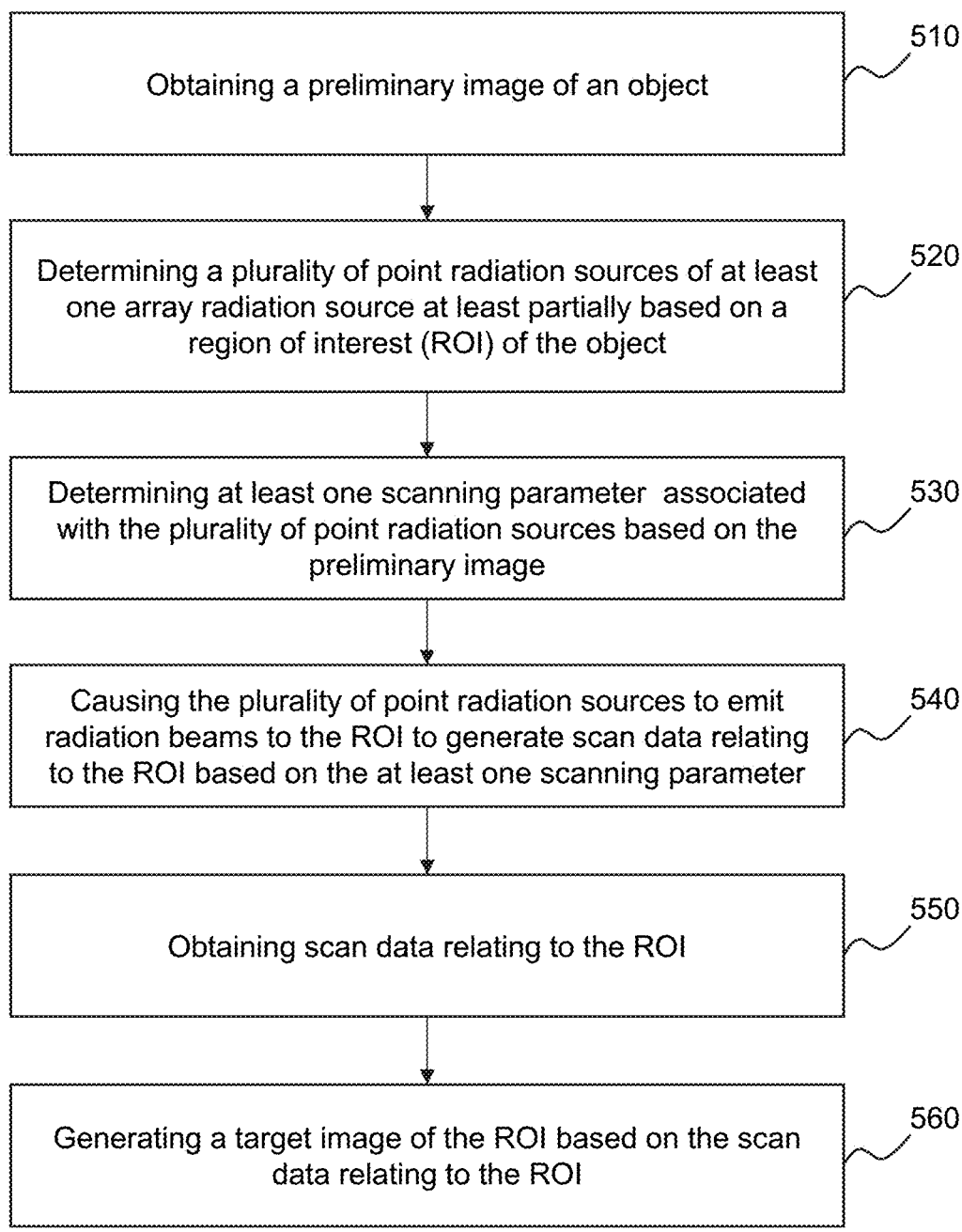
FIG. 5 is a flowchart illustrating an exemplary process for generating a target image of an ROI according to some embodiments of the present disclosure.

FIG. 5 is a flowchart illustrating an exemplary process for generating a target image of an ROI according to some embodiments of the present disclosure. In some embodiments, one or more operations of process 500 illustrated in FIG. 5 may be implemented in the imaging system 100 illustrated in FIG. 1. For example, the process 500 may be stored in a storage device (e.g., the storage device 150, the storage device 220, or the storage 390) of the imaging system 100 in the form of instructions, and invoked and/or executed by the processing device 140 (e.g., the processor 210 of the computing device 200 as illustrated in FIG. 2, the CPU 340 of the mobile device 300 as illustrated in FIG. 3, or one or more modules of the processing device 140 illustrated in FIG. 4).

In 510, the processing device 140 (e.g., the obtaining module 410) may obtain a preliminary image of an object.

The subject may include a biological object and/or a non-biological object. For example, the object may include a body of a patient. As another example, the object may include a specific portion of the patient, such as the upper limb, the abdomen, the head, the thorax, the breast, or the like, or a combination thereof.

In some embodiments, the preliminary image of the object may include but is not limited to an X-ray image of the object, an infrared image of the object, a microwave image of the object, an ultrasound image of the object, a nuclear magnetic resonance image of the object, a nuclide image of the object, a visible light image of the object, an impedance image of the object, or the like, or any combination thereof. The preliminary image of the object may be generated by various imaging devices. Exemplary imaging devices may include an X-ray imaging device (e.g., a CT scanner, a digital radiography (DR) device, an X-ray device, a DBT imaging device, an FFDM imaging device, etc.), an infrared imaging device, a microwave imaging device, an ultrasound imaging device, a nuclear magnetic resonance imaging device, a nuclide imaging device, a camera (e.g., a digital camera, an analog camera, a depth camera, a 3D scanner, etc.), an impedance imaging device, etc.

In some embodiments, the preliminary image of the object may be an image obtained when the object is in a state to be scanned. For example, the preliminary image may be an image of a patient to be scanned while the patient is positioned on a holder (e.g., the holder 115). In some embodiments, the preliminary image may be an image obtained when the object is in other states. For example, the preliminary image may be an image captured by a camera when the patient to be scanned enters a scanning room.

In some embodiments, the processing device 140 may cause at least a portion of a plurality of point radiation sources to emit radiation beams to the object to generate scan data relating to the object. In some embodiments, the processing device 140 may generate the preliminary image based on the scan data relating to the object.

In some embodiments, the preliminary image of the object may be generated by performing a pre-scanning (e.g., a CT scanning, an MR scanning, a PET scanning, a DR scanning, a DBT scanning, an FFDM scanning, or the like, or a combination thereof) on the object. For example, the preliminary image of the object may be acquired by an X-ray imaging device before the object is scanned. In some embodiments, the X-ray imaging device may use a portion or all of point radiation sources of at least one array radiation source to emit radiation beams to the object to obtain the preliminary image of the object. The point radiation source(s) may be predetermined based on a body part of the object. For a specific portion of the patient, the preliminary image of the portion may be acquired using one or more predetermined point radiation sources. Merely by way of example, if the object is the breast of a patient, the processing device 140 may select one or more point radiation sources predetermined for scanning the breast of the patient. As another example, if the object is the hand of a patient, the processing device 140 may select one or more point radiation sources predetermined for scanning the hand of the patient. In some embodiments, the X-ray imaging device may scan the object using all the point radiation sources of the at least one array radiation source with a relatively low radiation dose. In some embodiments, the radiation doses of the point radiation source(s) in the pre-scanning may be determined manually by a user of the terminal 130 (e.g., a doctor or a technician), or automatically by the processing device 140, or semi-automatically by the user of the terminal 130 and the processing device 140.

In some embodiments, the processing device 140 may obtain the preliminary image of the object from one or more components of the imaging system 100. For example, the processing device 140 may obtain the preliminary image of the object from the imaging device 110. As another example, the processing device 140 may obtain scan data relating to the object and generate the preliminary image based on the scan data. As still another example, the processing device 140 may obtain the preliminary image of the object from a storage device (e.g., the storage device 150, the storage device 220, or the storage 390) of the imaging system 100 via a network (e.g., the network 120). As a further example, the processing device 140 may obtain the preliminary image of the object from an external source (e.g., a medical database) via a network (e.g., the network 120).

In 520, the processing device 140 (e.g., the radiation determination module 420) may determine a plurality of point radiation sources of at least one array radiation source at least partially based on a region of interest (ROI) of the object.

An ROI of an object refers to at least one target portion of the object to be scanned or treated by an imaging device (e.g., the imaging device 110). For example, if the preliminary image is an image of a patient's body, the ROI may include a specific organ, a specific tissue, or the whole body of the patient presented in the preliminary image. As another example, if the preliminary image is an image of a specific portion of a patient's body, the ROI may include a lesion region of the specific portion of the patient's body. Merely by way of example, the preliminary image may be an image of the breast of the patient, and the ROI may include a cancer region, a lump region, a hydrops region, a node region, or the like, of the breast. In some embodiments, the ROI may be determined manually by a user of the terminal 130 (e.g., a doctor or a technician), automatically by the processing device 140, or semi-automatically by the user of the terminal 130 and the processing device 140. For example, the processing device 140 may determine the ROI of the object using an image recognition algorithm. The image recognition algorithm may include but not limited to a threshold-based segmentation, a histogram-based algorithm, a pattern recognition algorithm, an image match algorithm, a template matching algorithm, a target tracking algorithm, an artificial intelligence (AI) algorithm (e.g., a machine learning algorithm, such as a deep learning algorithm (e.g., a Region Convolutional Neural Networks (RCNN), a fast RCNN algorithm, a Single Shot Detection (SSD) algorithm, a RetinaNet algorithm, a You Only Look Once (YOLO) algorithm, etc.)), or the like, or any combination thereof. As another example, the processing device 140 may determine a region including the object and a region excluding the object in the preliminary image, and designate the region including the object as the ROI. As used herein, the region including the object refers to a human body that needs to be scanned or treated by the imaging device, while the region excluding the object refers to a region in the preliminary image which does not include the human body. For example, the region excluding the object may include a scanning table region, an environment region, a background region, or the like, or any combination thereof.

In some embodiments, the processing device 140 may determine the region including the object from the preliminary image using an aforementioned image recognition algorithm.

In some embodiments, the processing device 140 may recognize a target region of the object and designate the target region as the ROI. The target region in the preliminary image may correspond to a target portion of the object to be scanned or treated. For example, the target region may include an abdomen region, a chest region, a brain region, a heart region, a lung region, a tumor region, or the like, of the object. In some embodiments, the processing device 140 may determine the ROI based on the target region. For example, if the target region is the elbow joint region of a patient, then the ROI may be the elbow joint region or a region including the elbow joint region (e.g., a radiation region of one or more point radiation sources, an upper limb region, etc.). In some embodiments, the target region may be determined manually by a user of the terminal 130 (e.g., a doctor or a technician), or automatically by the processing device 140, or semi-automatically by the user of the terminal 130 and the processing device 140. For example, the processing device 140 may recognize the target region using an image recognition algorithm such as a threshold-based recognition algorithm, an edge-based recognition algorithm, a region-based recognition algorithm, a clustering-based algorithm, a wavelet transform-based recognition algorithm, a mathematical morphology-based recognition algorithm, an artificial neural network algorithm, etc.

In some embodiments, the processing device 140 may determine the plurality of point radiation sources from the at least one array radiation source. The plurality of point radiation sources may be used to emit radiation beams to the ROI of the object, while other point radiation sources of the at least one array radiation source excluding the plurality of point radiation sources may not emit radiation beams to the ROI of the object. In some embodiments, the processing device 140 may determine the plurality of point radiation sources of at least one array radiation source based on one or more factors such as at least one first parameter associated with each point radiation source of the at least one array radiation source, at least one second parameter associated with the ROI, an imaging requirement, or the like, or any combination thereof. More descriptions regarding the determination of the plurality of point radiation sources may be found elsewhere in the present disclosure. See, e.g., FIG. 6 and the relevant descriptions thereof.

In 530, the processing device 140 (e.g., the radiation determination module 420) may determine at least one scanning parameter associated with the plurality of point radiation sources based on the preliminary image.

In some embodiments, the at least one scanning parameter associated with the plurality of point radiation sources may include a radiation dose of each of the plurality of point radiation sources, a radiation angle of each of the plurality of point radiation sources, a radiation intensity of each of the plurality of point radiation source, a radiation time of each of the plurality of point radiation sources, a count of the plurality of point radiation sources, a radiation sequence of the plurality of point radiation sources, or the like, or any combination thereof.

The radiation intensity refers to a radiant flux (e.g., radiation energy emitted per unit time) emitted by a point radiation source per unit solid angle. In some embodiments, the radiation intensity may relate to a tube voltage and/or a tube current of the point radiation source. The tube voltage refers to a voltage between a cathode of the radiation source 112 and an anode of the radiation source 112 during the radiation source 112 is emitting radiation beams. The tube current refers to a current between the cathode of the radiation source 112 and the anode of the radiation source 112 during the radiation source 112 is emitting the radiation beams. The radiation dose corresponding to a region (e.g., an ROI) refers to the amount of radiation energy that is planned to be delivered to a portion of the subject corresponding (or substantially corresponding) to the region. In some embodiments, the radiation dose may be associated with the radiation intensity, SOD, the radiation time, etc. The radiation time refers to a period that the radiation source 112 emitting the radiation beams. The radiation sequence of the plurality of point radiation sources refers to a sequence or an order that the plurality of point radiation sources emit radiation beams. For example, two or more point radiation sources may emit radiation beams sequentially, synchronously, not synchronously, or according to other orders.

In some embodiments, the processing device 140 may determine the at least one scanning parameter based on at least one second parameter associated with the ROI. The second parameter associated with the ROI may include a thickness of the ROI, an attenuation characteristic of the ROI, a shape of the ROI, a position of the ROI, a size of the ROI, or the like, or any combination thereof. In some embodiments, the processing device 140 may determine the at least one scanning parameter based on the thickness (e.g., an absolute thickness, an equivalent thickness, etc.) of the ROI and/or the attenuation characteristic of the ROI. In some embodiments, the at least one scanning parameter may have a positive correlation with the at least one second parameter associated with the ROI. Specifically, if the thickness of the ROI is relatively large, the radiation dose may be relatively large. If the attenuation characteristic of the ROI is relatively large, the radiation dose may be relatively large. Merely by way of example, the plurality of point radiation sources may emit radiation beams to a lung and a bone of a human body. Because the attenuation characteristic of the bone is greater than that of the lung, the radiation dose for the bone may be greater than that for the lung to obtain images meeting the same imaging requirement.

In some embodiments, the processing device 140 may determine a first relationship between the radiation dose and the thickness of the ROI based on experimental data or data generated in actual applications. For example, the processing device 140 may obtain historical radiation doses and historical thicknesses of the ROI of a plurality of historical patients. The processing device 140 may determine the first relationship based on the historical radiation dose and the historical thicknesses of the ROI. In some embodiments, the first relationship may be determined based on reference radiation doses used to scan reference object(s) (associated with the object) and thicknesses of the reference object(s). The reference object(s) may include one or more phantoms. A phantom refers to an object which may have the same (or similar) characteristics (e.g., a thickness, an attenuation characteristic, a size, etc.) as (or to) that of a biological object. The first relationship may be represented by a curve, an equation, a function, a table, etc. The processing device 140 may determine the radiation dose based on the thickness of the ROI and the first relationship.

In some embodiments, the determination of the radiation dose based on the attenuation characteristic of the ROI may be the same as or similar to the determination of the radiation dose based on the thickness of the ROI. For example, the processing device 140 may determine a second relationship between the radiation dose and the attenuation characteristic of the ROI, e.g., based on historical radiation doses and historical attenuation characteristics of the ROI. As another example, the processing device 140 may determine the second relationship between the radiation dose and the attenuation characteristic of the ROI based on reference radiation dose(s) used to scan reference object(s) (associated with the object) and attenuation characteristic(s) of the reference object(s). The processing device 140 may determine the radiation dose based on the attenuation characteristic of the ROI and the second relationship.

In some embodiments, the processing device 140 may determine the at least one scanning parameter by adjusting at least one reference scanning parameter used to scan the reference object(s) associated with the object. Merely by way of example, if the ROI is a breast of a patient, the processing device 140 may determine an average glandular dose (AGD) of the breast by adjusting a reference radiation dose used to scan the reference object.

In some embodiments, the processing device 140 may determine the at least one scanning parameter based on the at least one second parameter associated with the ROI, the imaging requirement, etc. For example, the processing device 140 may determine different scanning parameters for scanning or treating different ROIs. The processing device 140 may determine a relatively large radiation dose, a relatively long radiation time, a relatively large radiation intensity, and/or a relatively large count of point radiation sources, or the like, for an ROI with a relatively large thickness (and/or attenuation characteristic). As yet another example, if the imaging requirement of the ROI is relatively high (e.g., a resolution of a target image is relatively high, sharpness of the target image is relatively high, a noise of the target image is relatively low, etc.), the processing device 140 may determine a relatively large radiation dose, a relatively long radiation time, a relatively large radiation intensity, and/or a relatively large count of point radiation sources, or the like, or any combination thereof.

In some embodiments, for a specific tube voltage and a specific thickness, the processing device 140 may determine a third relationship between the radiation dose (e.g., the product of the tube current and the radiation time) and the imaging requirement (e.g., the gray value of the target image of the ROI) using the historical radiation doses and historical images of the historical patients. In some embodiments, the third relationship between the radiation dose and the imaging requirement may be determined based on reference radiation dose(s) used to scanning the reference object(s) (associated with the object) and imaging requirement(s) of a plurality of reference images generated by scanning the reference object(s). The processing device 140 may determine the radiation dose based on the third relationship and the imaging requirement.

In some embodiments, historical scan data of different patients or different portions may be stored in the storage device (e.g., the storage device 150, the storage device 220 of the computing device 200, the storage 390, or an external storage device). The processing device 140 may determine a similarity degree between a current patient and the historical patient(s). For example, the processing device 140 may compare patient information (e.g., an age, gender, obesity, a thickness (e.g., an equivalent thickness), an attenuation characteristic, information associated with an ROI, etc.) of the current patient with that of the historical patient(s). The processing device 140 may select a candidate historical patient with the highest similarity with the current patient. The processing device 140 may adjust at least one scanning parameter associated with a plurality of historical point radiation sources that emitted radiation beams to the historical patient(s) to obtain the at least one scanning parameter associated with the plurality of point radiation sources of the at least one array radiation source. For example, the processing device 140 may determine a ratio of the thickness of the ROI of the current patient to the thickness of the ROI of the historical patient, and determine the radiation dose of the plurality of point radiation sources by multiplying a radiation dose of the plurality of historical point radiation sources and the ratio. More descriptions regarding the determination of the scanning parameter associated with each point radiation source of the at least one array radiation source may be found elsewhere in the present disclosure. See, e.g., FIG. 6 and the relevant descriptions thereof.

In 540, the processing device 140 (e.g., the radiation control module 430) may cause the plurality of point radiation sources to emit radiation beams to the ROI to generate scan data relating to the ROI based on the at least one scanning parameter.

In some embodiments, the processing device 140 may cause the plurality of point radiation sources to emit radiation beams in various manners (e.g., a radiation starting time, a radiation duration time, etc., of each of the plurality of point radiation sources may be determined). For example, the processing device 140 may divide the plurality of point radiation sources into one or more groups (e.g., based on the first parameter associated with each of the plurality of point radiation sources and the at least one second parameter associated with the ROI), and radiation regions of each group of point radiation sources may have no overlapping region. A radiation region of a radiation source (e.g., a point radiation source) refers to a region on a detector, which is irradiated by radiation beams emitted by the radiation source. For illustration purposes, the radiation region on the detector may be described as an example in the present disclosure. In some embodiments, the radiation region of the radiation source on other planes (e.g., the plane where the ROI locates) may be determined based on the radiation region on the detector (e.g., based on at least one first parameter associated with each point radiation source, at least one second parameter associated with the ROI, etc.).

In some embodiments, the processing device 140 may optimize the number or count of the groups of the plurality of point radiation sources and the number or count of point radiation sources in each of the one or more groups, e.g., using an iterative algorithm.

In some embodiments, the processing device 140 may cause the one or more groups of point radiation sources to emit radiation beams sequentially. In some embodiments, the processing device 140 may cause at least two point radiation sources in one or more (e.g., each) of the groups of point radiation sources to synchronously emit radiation beams. For example, a group of point radiation sources may include two or more point radiation sources, and the processing device 140 may cause at least two point radiation sources in the group to synchronously emit radiation beams. In some embodiments, the processing device 140 may cause all the point radiation sources in a group to synchronously emit radiation beams. In some embodiments, at least two point radiation sources of a group may be non-adjacent such that radiation regions of the at least two point radiation sources have no overlapping region. As used herein, two point radiation sources are non-adjacent refers to that the at least one array radiation source may include a third point radiation source, and a distance between the third point radiation source and at least one of the two point radiation sources may be less than a distance between the two point radiation sources. Take the array radiation source 700 as an example, a distance D1 is formed between a point radiation source 711 and a point radiation source 712, a distance D2 is formed between the point radiation source 711 and a point radiation source 722, and a distance D3 is formed between the point radiation source 712 and the point radiation source 722. If the distance D1 is less than D2 and the distance D3 is less than the distance D2, the point radiation source 711 and the point radiation source 722 may be regarded as non-adjacent. On this occasion, because at least two non-adjacent point radiation sources are caused to synchronously emit radiation beams, and the corresponding radiation regions do not overlap (i.e., have no overlapping region) in scanning the object, artifacts (e.g., artifacts caused by the overlapping region) of a target image of the ROI reconstructed based on the scan data may be reduced or eliminated.

As yet another example, the processing device 140 may cause the plurality of point radiation sources to emit radiation beams in different modes (e.g., radiation intensities of the plurality of point radiation source may be different, a state of the object (e.g., whether the object is injected with a contrast agent) may be various, etc.). Exemplary modes may include a mode in which the radiation beams emitted to the ROI have relatively high energy (also referred to as a high energy mode), a mode in which the radiation beams emitted to the ROI have relatively low energy (also referred to as a low energy mode), a mode in which the object is injected with a contrast agent, a mode in which the object is injected with no contrast agent, etc. Merely by way of example, the processing device 140 may cause the plurality of point radiation sources to emit radiation beams to the ROI in a low energy mode in which the radiation beams may have energy E1, the processing device 140 may cause the plurality of point radiation sources to emit radiation beams in a high energy mode in which the radiation beams may have energy E2, and the energy E2 may be greater than the energy E1. More descriptions regarding the radiation of the plurality of point radiation sources may be found elsewhere in the present disclosure. See, e.g., FIG. 10, and the relevant descriptions thereof.

In 550, the processing device 140 (e.g., the obtaining module 410) may obtain scan data relating to the ROI.

The scan data may be used to generate one or more images associated with the ROI. In some embodiments, the scan data may include raw data (e.g., projection data), image data (e.g., an image slice), PET data (e.g., gamma photon information), SPECT data (e.g., gamma photon information), MR data (e.g., echo signals), CT data (e.g., projection data), or the like, or any combination thereof. In some embodiments, the scan data may be two-dimensional (2D) scan data, three-dimensional (3D) scan data, four-dimensional (4D) scan data, or the like, or any combination thereof.

In some embodiments, the ROI may include a plurality of sub-regions. The scan data may include a plurality of pieces of data corresponding to the plurality of sub-regions of the ROI. The processing device 140 may obtain the plurality of pieces of data when the plurality of point radiation sources emit radiation beams to the ROI. In some embodiments, the processing device 140 may obtain a first set of data when the plurality of point radiation sources emit radiation beams to the ROI in a first mode. The processing device 140 may obtain a second set of data when the plurality of point radiation sources emit radiation beams to the ROI in a second mode. The processing device 140 may obtain a first portion of the scan data by combining the first set of data. The processing device 140 may obtain a second portion of the scan data by combining the second set of data. Alternatively, the processing device 140 may obtain the scan data by fusing the first portion of the scan data and the second portion of the scan data. More descriptions regarding the obtaining of the scan data may be found elsewhere in the present disclosure. See, e.g., FIG. 10 and the relevant descriptions thereof.

In some embodiments, the processing device 140 may obtain the scan data from the imaging device 110. Alternatively, the scan data may be acquired by the imaging device 110 and stored in a storage device (e.g., the storage device 150, the storage device 220 of the computing device 200, the storage 390, or an external storage device). The processing device 140 may retrieve the scan data from the storage device.

In 560, the processing device 140 (e.g., the image generation module 440) may generate a target image of the ROI based on the scan data relating to the ROI.

In some embodiments, a type of the target image of the ROI may be the same as or different from that of the preliminary image. The target image may include, but is not limited to, an X-ray image, a computer tomography (CT) image, an FFDM, a DBT image, a PET image, a SPECT image, an MR image, an ultrasound scan (US) image, a color doppler blood flow imaging (CDFI) image, a DSA image, a magnetic resonance angiography (MRA) image, a time-of-flight magnetic resonance image (TOF-MRI), or a magnetoencephalography (MEG) image. In some embodiments, the target image may include a 2D image, a 3D image, etc. In some embodiments, the 3D image may include a series of 2D slice images or layer images.

In some embodiments, the processing device 140 may generate the target image based on the scan data using an image reconstruction technique. The image reconstruction technique may include an iterative reconstruction algorithm (e.g., a statistical reconstruction algorithm), a Fourier slice theorem algorithm, a fan-beam reconstruction algorithm, an analytic reconstruction algorithm (e.g., a filtered back projection (FBP) algorithm), an algebraic reconstruction technique (ART), a simultaneous algebra reconstruction technique (SART), a Feldkamp-Davis-Kress (FDK) reconstruction technique, or the like, or any combination thereof.

In some embodiments, the processing device 140 may determine one or more images based on at least a portion of the scan data, and generate the target image based on the one or more images. For example, the processing device 140 may determine a first image based on the first portion of the scan data, and determine a second image based on the second portion of the scan data. The processing device 140 may generate the target image by fusing the first image and the second image. As another example, the processing device 140 may generate a plurality of images based on the plurality of pieces of data corresponding to the plurality of sub-regions of the ROI. The processing device 140 may generate the target image by stitching the plurality of images.

Alternatively, the processing device 140 may process the scan data and generate the target image based on the scan data and/or the processed scan data. For example, the processing device 140 may process the scan data to obtain data associated with the contrast agent. The processing device 140 may generate the target image based on the scan data and the data associated with the contrast agent, thereby improving the resolution of the target image. More descriptions regarding the generation of the target image may be found elsewhere in the present disclosure. See, e.g., FIG. 10, and the relevant descriptions thereof.

It should be noted that the above description regarding the process 500 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. The operations of the illustrated process 500 are intended to be illustrative. In some embodiments, the process 500 may be accomplished with one or more additional operations not described, and/or without one or more of the operations discussed. For example, during or after operation 560, the process 500 may include an operation for processing the target image. The processing of the target image may include a distortion adjustment, a color adjustment, a grayscale adjustment, or the like, or any combination thereof.

Figure 6:
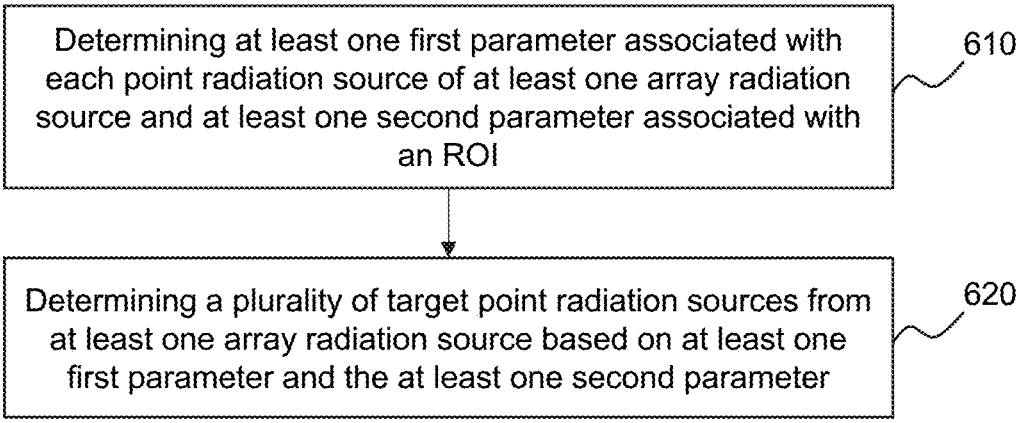
FIG. 6 is a flowchart illustrating an exemplary process for determining a plurality of point radiation sources from at least one array radiation source according to some embodiments of the present disclosure.

FIG. 6 is a flowchart illustrating an exemplary process for determining a plurality of point radiation sources from at least one array radiation source according to some embodiments of the present disclosure. In some embodiments, the process 600 may be an exemplary embodiment of operation 520 as described in connection with FIG. 5. In some embodiments, one or more operations of process 600 illustrated in FIG. 6 may be implemented in the imaging system 100 illustrated in FIG. 1. For example, the process 600 may be stored in a storage device (e.g., the storage device 150, the storage device 220, or the storage 390) of the imaging system 100 in the form of instructions, and invoked and/or executed by the processing device 140 (e.g., the processor 210 of the computing device 200 as illustrated in FIG. 2, the CPU 340 of the mobile device 300 as illustrated in FIG. 3, or one or more modules of the processing device 140 illustrated in FIG. 4).

In 610, the processing device 140 (e.g., the radiation determination module 420) may determine at least one first parameter associated with each point radiation source of at least one array radiation source and at least one second parameter associated with an ROI.

Figure 7:
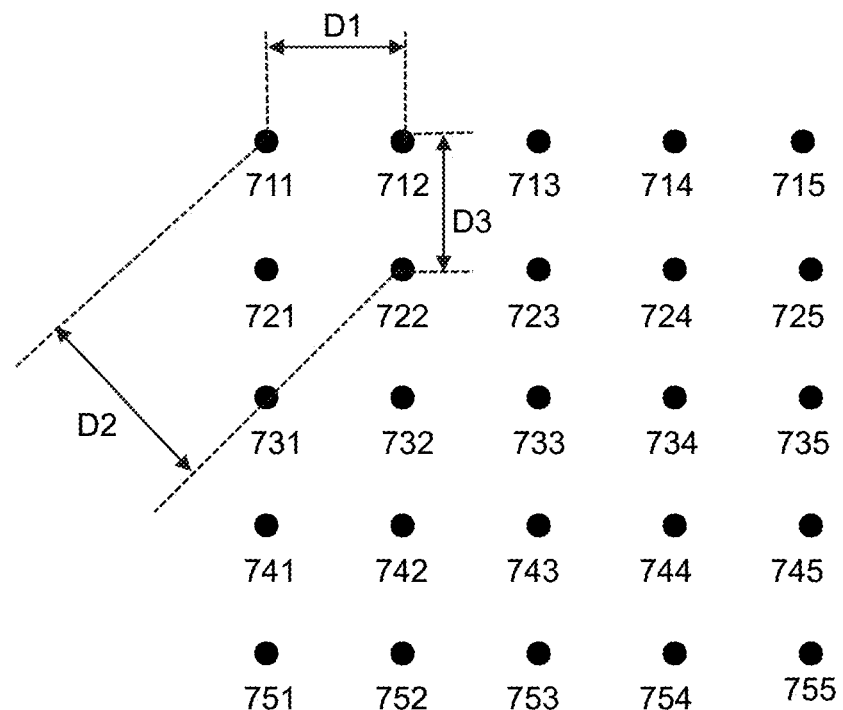
FIG. 7 is a schematic diagram illustrating an exemplary array radiation source according to some embodiments of the present disclosure.

In some embodiments, each of the at least one array may include a plurality of point radiation sources. For illustration purposes, FIG. 7 is a schematic diagram illustrating an exemplary array radiation source 700 according to some embodiments of the present disclosure. As shown in FIG. 7, the array radiation source 700 has a planar arrangement. The array radiation source 700 includes twenty five point radiation sources (i.e., point radiation sources 711, 712, . . . , 715, 721, 722, . . . , 725, 731, 732, . . . , 735, 741, 742, . . . , 745, 751, 752, . . . , 755) each of which is represented by a solid pot. The point radiation sources are arranged in five rows and five columns. Each row includes five point radiation sources, and each column includes five point radiation sources.

In some embodiments, the point radiation sources of the at least one array radiation source may be arranged in various shapes, such as a square, a rectangle, a triangle, a polygon, a circle, an ellipse, an irregular shape, or the like. In some embodiments, the number (or the count) of the point radiation sources may be determined according to actual imaging needs. Specifically, the number (or the count) of the point radiation sources may relate to a size of the ROI, a thickness of the ROI, an attenuation characteristic of the ROI, a required radiation dose of the point radiation source, an imaging requirement, or the like, or any combination thereof. Merely by way of example, if an ROI of the object to be scanned or treated by the at least one array radiation source is relatively large, the number (or count) of point radiation sources may be relatively large, or vice versa. In some embodiments, the number (or the count) of point radiation sources in the array radiation source 700 may be set according to actual conditions, such as 3, 5, 8, 10, 25, etc.

In some embodiments, the plurality of point radiation sources of the at least one array radiation source may be arranged uniformly or non-uniformly. In some embodiments, the arrangement density of point radiation sources of the array radiation source may be indicated by a number (or count) of point radiation sources per unit area. For example, the number of point radiation sources per unit area may be different across different regions of the array radiation source. In some embodiments, the arrangement density of point radiation sources of the array radiation source may be indicated by a distance between each two adjacent point radiation sources. For example, as shown in FIG. 7, distances between any two adjacent point radiation sources in the array radiation source 700 may be equal.

In some embodiments, the at least one first parameter associated with each point radiation source may include a source-to-image distance (SID), a source-to-object distance (SOD), a position, a radiation region, or the like, of the each point radiation source. The SID refers to a distance between a point radiation source to a detector (e.g., the detector 116) of an imaging device (e.g., the imaging device 110). The SOD refers to a distance between a point radiation source to the object. In some embodiments, the SOD may be indicated by a distance between the point radiation source and a physical point (e.g., a center point) of the ROI. The position of a point radiation source refers to a position of the point radiation source in the at least one array radiation source. In some embodiments, the position of the point radiation source may include an absolute position of the point radiation source or a relative position of the point radiation source with respect to a reference point (e.g., another point radiation source, a point in the scanning table, etc.). In some embodiments, the SID, the SOD, and/or the positions of each point radiation source may be determined based on a geometric position relationship between e.g., a radiation source (e.g., the radiation source 112), a detector (e.g., the detector 116), a holder (e.g., the holder 115), and/or a position of the object. In some embodiments, the SID, the SOD, and/or the positions of each point radiation source may be determined by a user of the terminal 130 (e.g., a doctor or a technician), or automatically by the processing device 140, or semi-automatically by the user of the terminal 130 and the processing device 140.

The radiation region of a point radiation source refers to a region on the detector which receives radiation beams that are emitted by the point radiation source and pass through the object. In some embodiments, the at least one first parameter may be predetermined and stored on a storage device (e.g., the storage device 150, the storage device 220 of the computing device 200, or the storage 390). For example, the processing device 140 may control the plurality of point radiation sources to emit radiation beams to determine the radiation region of the each point radiation source when the object is not placed on the scanning table.

Figure 12:
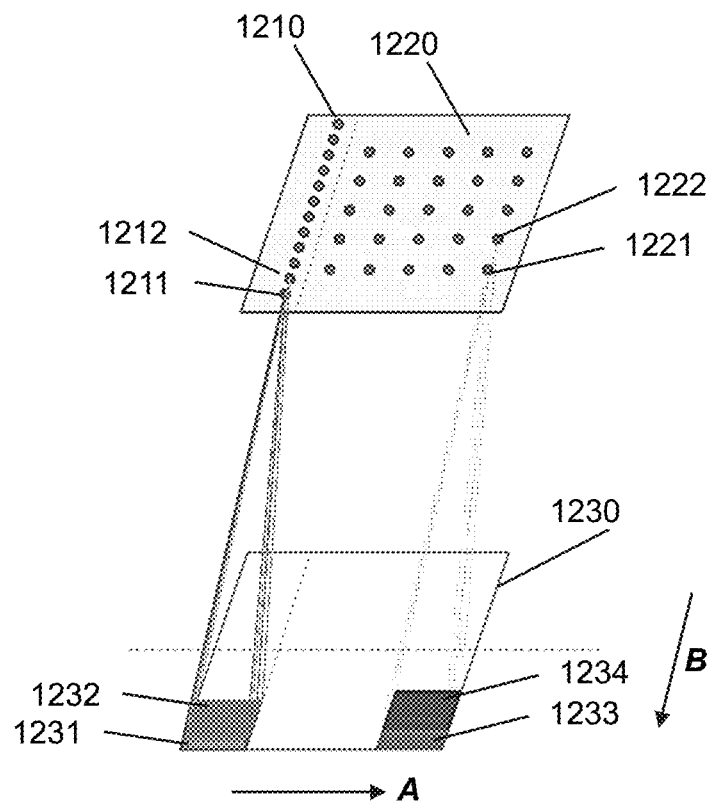
FIG. 12 is a schematic diagram illustrating exemplary array radiation sources according to some embodiments of the present disclosure.

For illustration purposes, FIG. 12 is a schematic diagram illustrating exemplary array radiation sources according to some embodiments of the present disclosure. As shown in FIG. 12, the array radiation sources may include an array radiation source 1210 having a linear arrangement and an array radiation source 1220 having a planar arrangement. Each of the array radiation source 1210 and the array radiation source 1220 includes a plurality of point radiation sources, and each of the plurality of point radiation sources corresponds to a radiation region on a detector 1230. For example, a point radiation source 1211 of the array radiation source 1210 corresponds to a radiation region 1231, a point radiation source 1212 of the array radiation source 1210 corresponds to a radiation region 1232, a point radiation source 1221 of the array radiation source 1220 corresponds to a radiation region 1233, and a point radiation source 1222 of the array radiation source 1220 corresponds to a radiation region 1234.

The at least one second parameter associated with the ROI may include a thickness of the ROI, an attenuation characteristic of the ROI, a shape of the ROI, a position of the ROI, a size of the ROI, or the like, or any combination thereof.

In some embodiments, the thickness of the ROI may include a thickness of a feature point (or a pixel) corresponding to a portion of the ROI, an average thickness of the ROI, a maximum thickness of the ROI, etc. In some embodiments, the thickness of the ROI may include an absolute thickness, an equivalent thickness, etc. The absolute thickness of the ROI refers to a traveling distance that the radiation beams emitted by the point radiation source(s) through the ROI when the ROI is radiated by the radiation beams. For example, if the ROI is the chest of a patient, the absolute thickness of the ROI may be the distance from the front chest to the back of the patient. The equivalent thickness refers to a thickness of a first reference object (e.g., a phantom) that may have attenuation characteristics (to the radiation beams) the same as or similar to that of the ROI. The first reference object may include a water phantom, a polymethyl methacrylate (PMMA) phantom, etc. Correspondingly, the equivalent thickness may include a water equivalent thickness (WET), a PMMA equivalent thickness, etc.

In some embodiments, the position of the ROI may be represented by a coordinate in a coordinate system (e.g., the coordinate system 160).

The attenuation characteristic of the ROI may indicate an absorption property of the ROI to radiation beams emitted by the point radiation source(s). The attenuation characteristic of the ROI may be related to the intensity of the radiation beams emitted by the point radiation source(s), the thickness of the ROI, the density of the ROI, whether the ROI includes an implant (e.g., a metal), etc. For example, the density of human bones is greater than that of fat tissue, and under a same radiation condition, the attenuation characteristic of the human bones is greater than that of the fat tissue. In some embodiments, the attenuation characteristic may be expressed by an attenuation coefficient. In some embodiments, the attenuation coefficient of the ROI may include absolute attenuation coefficient, equivalent attenuation coefficient, etc. The absolute attenuation coefficient refers to a difference between an intensity of the radiation beams emitted by the point radiation source(s) and an intensity of radiation beams that pass through the ROI. In some embodiments, the attenuation coefficient of the ROI may be represented by a curve, an equation, a table, etc., for example, the Beer-Lambert Law. The equivalent attenuation coefficient of the ROI refers to an attenuation coefficient of a second reference object (e.g., a phantom) that may have attenuation characteristics (to the radiation beams) the same as or similar to that of the ROI. The second reference object may be the same as or similar to the first reference object.

In some embodiments, the processing device 140 may determine the second parameter associated with the ROI based on the preliminary image.

The processing device 140 may determine the thickness of the ROI based on various techniques. For example, if the preliminary image is captured by a camera, the thickness of the ROI may be determined using an optical technique. In some embodiments, if the preliminary image is captured by a 3D camera, one or more 2D cameras, a 2D camera with a distance sensor, etc., the thickness of the ROI may be determined based on a structured light (e.g., ORBBEC structured light) technique, an optical TOF technique, a binocular stereo vision technique, etc. As another example, the processing device 140 may obtain a plurality of reference images by scanning reference objects with different thicknesses (e.g., a plurality of first reference objects with different thicknesses, a plurality of second reference objects with different thicknesses), and determine a relationship between gray values of the plurality of reference images and the thicknesses of the reference objects. The processing device 140 may retrieve a thickness of the reference object based on the gray value of the preliminary image and the relationship between the gray values of the plurality of reference images and the thicknesses of the reference objects, and designate the thickness of the reference object corresponding to the gray value of the preliminary image as the thickness of the ROI.

The determination of the attenuation coefficient of the ROI may be similar to the determination of the thickness of the ROI. For example, the processing device 140 may obtain a plurality of reference images by scanning reference objects with different attenuation coefficients (e.g., a plurality of third reference objects with different attenuation coefficients, a plurality of fourth reference objects with different attenuation coefficients), and determine a relationship between gray values of the plurality of reference images and the attenuation coefficients of the reference objects. The processing device 140 may retrieve an attenuation coefficient of the reference object based on the gray value of the preliminary image and the relationship between the gray values of the plurality of reference images and the attenuation coefficients of the reference objects, and designate the attenuation coefficient of the reference object corresponding to the gray value of the preliminary image as the attenuation coefficient of the ROI.

In 620, the processing device 140 (e.g., the radiation determination module 420) may determine a plurality of point radiation sources based on at least one first parameter associated with each point radiation source of the at least one array radiation source and at least one second parameter associated with the ROI.

In some embodiments, the processing device 140 may determine the plurality of target point radiation sources radiation regions of which may cover the ROI as the plurality of target point radiation sources. The plurality of target point radiation sources may emit radiation beams to the ROI, while the point radiation source(s) whose radiation regions do not cover the ROI may not emit radiation beams to the ROI, thereby reducing the radiation dose received by the object.

Figure 8:
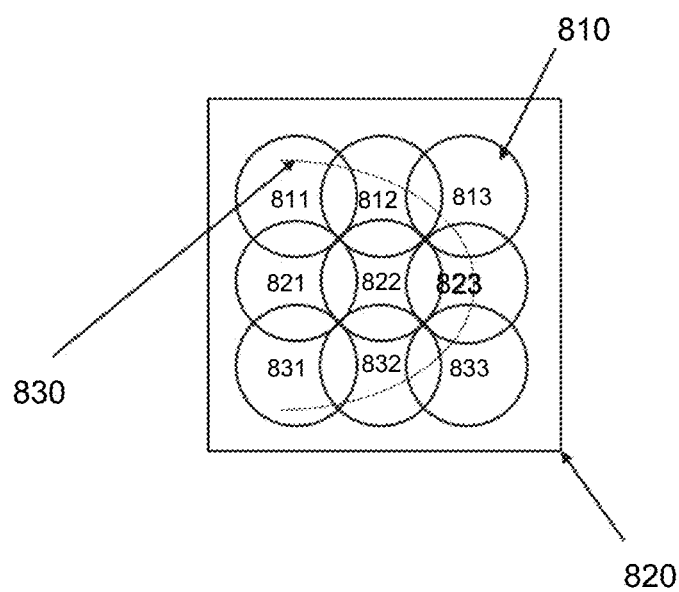
FIG. 8 is a schematic diagram illustrating a plurality of exemplary radiation regions according to some embodiments of the present disclosure.

In some embodiments, the processing device 140 may determine one or more groups of point radiation sources from the at least one array radiation source based on the radiation regions of each point radiation source. Radiation regions of the one or more groups of point radiation sources may cover the ROI. Radiation regions of each group of point radiation sources may have no overlapping region. For illustration purposes, FIG. 8 is a schematic diagram illustrating a plurality of exemplary radiation regions of point radiation sources according to some embodiments of the present disclosure. As shown in FIG. 8, 810 refers to radiation regions of a plurality of point radiation sources, 820 refers to a detector, and 830 refers to an ROI (e.g., the breast of a patient). The radiation regions 810 may cover the ROI 830, thereby improving the quality of a target image of the ROI 830. The radiation regions 810 may correspond to nine point radiation sources 811, 812, 813, 821, 822, 823, 831, 832, and 833, respectively. In some embodiments, the nine point radiation sources may be divided into one or more groups based on the radiation regions 810. For example, the nine point radiation sources may be divided into a group $A_1$ and a group $A_2$, the group $A_3$ may include the point radiation sources 811, 813, 822, 831, and 833, and the group $A_2$ may include the point radiation sources 812, 821, 823, and 832. As another example, the nine point radiation sources may be divided into a group $B_1$, a group $B_2$, and a group $B_3$, the group $B_1$ may include the point radiation source 811 and point radiation source 813, the group $B_2$ may include radiation sources 822, 831, and 833, and the group $B_3$ may include point radiation sources 812, 821, 823, and 832. As yet another example, the nine point radiation sources may be divided into a group $C_1$, a group $C_2$, a group $C_3$, a group $C_4$, and a group $C_5$, the group $C_1$ may include the point radiation source 811, the group $C_2$ may include the point radiation source 822 and the point radiation source 813, the group $C_3$ may include the point radiation source 831 and point radiation source 833, the group $C_4$ may include the point radiation source 812 and point radiation source 821, and the group $C_5$ may include the point radiation source 823 and point radiation source 832. Radiation regions of point radiation sources in each of the aforementioned groups may have no overlapping region.

In some embodiments, the processing device 140 may determine the plurality of radiation sources based on an imaging requirement. The imaging requirement may include an image resolution, an image gray, an image brightness, an image depth, a signal-to-noise ratio, or the like, or any combination thereof. The imaging requirement may be determined manually by a user of the terminal 130 (e.g., a doctor or a technician), or automatically by the processing device 140, or semi-automatically by the user of the terminal 130 and the processing device 140. For example, the processing device 140 may determine one or more sets of point radiation sources from the at least one array radiation source, and designate the set(s) of point radiation sources as the plurality of target point radiation sources such that the target image generated based on the radiation beams emitted by the target point radiation sources meets an imaging requirement. In some embodiments, the processing device 140 may determine, from the at least one array radiation source, one or more sets of point radiation sources, wherein radiation regions of each set of point radiation sources cover the ROI. In some embodiments, the processing device 140 may designate, among the one or more sets of point radiation sources, a target set of point radiation sources having a minimum count of point radiation sources as the plurality of point radiation sources. For example, if the target image generated based on the radiation beams emitted by two or more sets of point radiation sources meets the imaging requirement, the processing device 140 may designate set(s) of point radiation sources having a minimum count of point radiation sources as the plurality of target point radiation sources. In this case, the imaging requirement may be meet and the radiation dose received by the object may be reduced or minimized.

In some embodiments, the plurality of point radiation sources may be predetermined and information (e.g., positions, numbers, radiation sequence, groups, sets, etc.) regarding the point radiation sources may be stored in a storage device (e.g., the storage device 150, the storage device 220 of the computing device 200, the storage 390, or an external device). For example, for a specific portion (e.g., the hand) of a patient, the plurality of point radiation sources of the at least one array radiation source may be predetermined and information regarding the point radiation sources may be stored. The processing device 140 may retrieve the information regarding the plurality of point radiation sources from the storage device. As another example, the plurality of point radiation sources may be determined based on a predetermined rule. In some embodiments, for a specific organ of a patient, the plurality of point radiation sources may be determined and stored in the storage device. Merely by way of example, for the breast of a patient, the plurality of point radiation sources may be determined and the processing device 140 may retrieve the predetermined point radiation sources when the breast is to be scanned.

Figure 9:
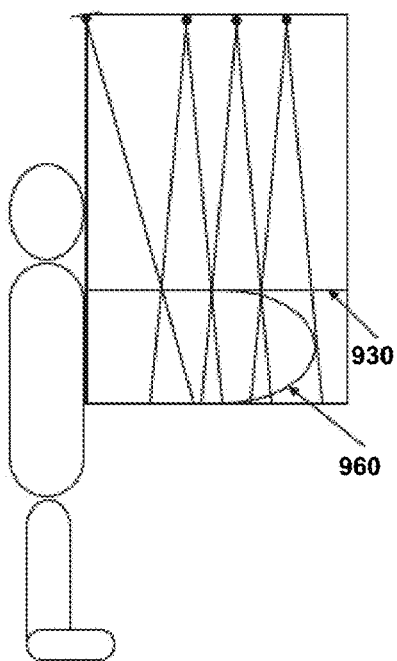
FIG. 9 is a schematic diagram illustrating an exemplary breast imaging according to some embodiments of the present disclosure.
Figure 9:
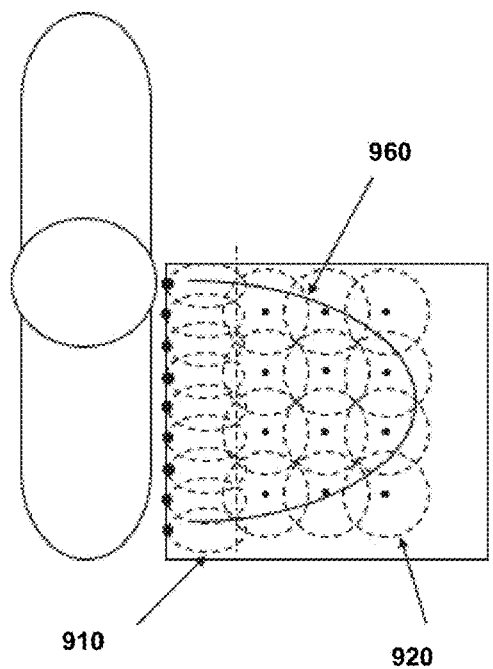

FIG. 9 is a schematic diagram illustrating exemplary breast imaging according to some embodiments of the present disclosure.

As shown in FIG. 9, 900 shows a side view of the breast imaging, and 950 shows a top view of the breast imaging. As shown in FIG. 9, 910 refers to a first region, 920 refers to a second region, 960 refers to the breast to be imaged, and 930 refers to a compression component. The first region 910 may be adjacent to a breast wall of the breast. The breast 960 is placed in the second region 920. The compression component 930 covers a top of the breast 960 to compress the breast 960 to cause the breast 960 to be far away from a radiation source of the imaging device and close to a detector, thereby improving the signal-to-noise ratio of an acquired image of the breast. Due to the structural characteristics of the breast, the breast may be of a tapered shape under a natural condition. The compression component 930 may average the height of the breast 960 in a vertical direction of the imaging device, thereby improving the uniformity of the gray level of the acquired image of the breast.

When the imaging device acquires the image of the breast, the body of the patient is standing on a side of the first region 910, the chest may be close to the first region 910, and the outside of the breast wall may face the second region 920. The breast wall refers to an area formed by the breastbone, ribs, and human tissue between the ribs. An inner side of the breast wall forms the chest cavity in which tissues and organs such as the heart, the lung, the spleen, the pancreas, etc., may be located. During the breast is scanned, radiation beams should be avoided to penetrate the breast wall and irradiate the tissues and organs across the breast wall.

In some embodiments, an array radiation source disposed in the first region 910 may have a linear arrangement. In some embodiments, the array radiation source disposed in the second region 920 may have a planar arrangement. Specifically, the array radiation source in the second region 920 may include an array with a regular shape (e.g., a circular, a square, a triangular), an irregular shape, or the like. The array radiation source with a regular shape in the second region 920 may facilitate the arrangement of the array radiation source, and improve the efficiency and accuracy of determining the radiation regions of one or more point radiation sources of the array radiation source. In some alternative embodiments, the array radiation source in the second region 920 may be arranged along a curve or on a curved surface.

One or more point radiation sources of an array radiation source in the first region 910 may be arranged in a straight line. In some embodiments, the point radiation sources of the array radiation source in the first region 910 may also be arranged in a non-linear manner. For example, the point radiation sources of the array radiation source in the first region 910 may be arranged based on a shape of the breast wall of the patient.

In some embodiments, the arrangement density of the point radiation sources in the first region 910 may be greater than that of the point radiation sources in the second region 920 in the direction parallel to the breast wall. Due to a relatively large tissue density near the breast wall of the human body, such design of the arrangement densities of the point radiation sources in the first region 910 and the second region 920 may improve the clarity of the image of the breast.

In some embodiments, the point radiation sources in the first region 910 may be tilted or deflected away from the breast wall and the radiation beams emitted by the point radiation sources in the first region 910 may rotate away from the breast wall such that an angle is formed between radiation beams emitted by the array radiation source in the first region 910 and radiation beams emitted by the array radiation source in the second region 920. In some embodiments, a direction of the radiation beams close to the breast wall in the first region 910 may be vertical to (or substantially vertical to) the compression component 930. In some embodiments, an angle formed between the direction of the radiation beams close to the breast wall in the first region 910 and the vertical direction of the compression component 930 may be not greater than an angle threshold (e.g., 1°, 2°, 5°, etc.). That is, an angle formed between the direction of the radiation beams close to the breast wall in the first region 910 and the compression component 930 may be in a range [89°, 91°], [88°, 92°], [85°, 95°], or the like, or any combination thereof. The radiation beams emitted by the point radiation sources may not pass through the breast wall, thereby reducing the radiation beams received by the patient and protecting the patient. In addition, the arrangement of the array radiation source in the first region 910 may ensure the radiation dose used to scan the region close to the breast wall.

Figure 10:
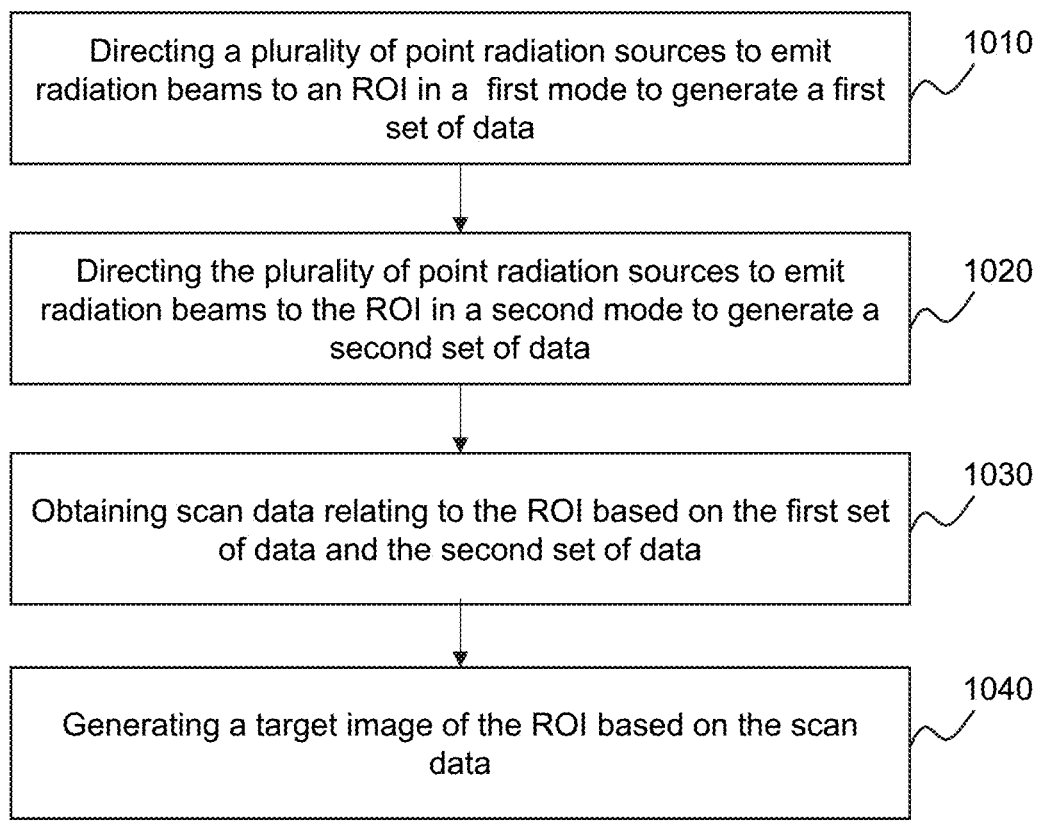
FIG. 10 is a flowchart illustrating an exemplary process for causing a plurality of point radiation sources to emit radiation beams to an ROI of an object in different modes according to some embodiments of the present disclosure.

FIG. 10 is a flowchart illustrating an exemplary process 1000 for causing a plurality of point radiation sources to emit radiation beams to an ROI of an object in different modes according to some embodiments of the present disclosure. In some embodiments, the process 1000 may be an exemplary embodiment of operation 540 as described in connection with FIG. 5. In some embodiments, one or more operations of process 1000 illustrated in FIG. 10 may be implemented in the imaging system 100 illustrated in FIG. 1. For example, the process 1000 may be stored in a storage device (e.g., the storage device 150, the storage device 220, or the storage 390) of the imaging system 100 in the form of instructions, and invoked and/or executed by the processing device 140 (e.g., the processor 210 of the computing device 200 as illustrated in FIG. 2, the CPU 340 of the mobile device 300 as illustrated in FIG. 3, or one or more modules of the processing device 140 illustrated in FIG. 4).

In 1010, the processing device 140 (e.g., the radiation control module 430) may direct the plurality of point radiation sources (e.g., the target point radiation sources determined in 620) to emit radiation beams to the ROI in a first mode to generate a first set of data.

In some embodiments, the first mode may include a high energy mode, a low energy mode, a mode in which the object is injected with a contrast agent, a mode in which the object is not injected with the contrast agent, or the like, or any combination thereof.

In some embodiments, an energy mode may be generated or realized by determining, adjusting, or using a tube voltage, a target of a radiation source (e.g., the radiation source 112), a filter of a collimator of the imaging device, or the like, or any combination thereof. Exemplary materials of the target may include tungsten, rhenium, molybdenum, platinum, rhodium, tantalum, niobium, chromium-molybdenum, germanium, hungry, iridium, palladium, scandium, technetium, or the like, or any combination thereof. The filter may be configured to reduce or eliminate specific radiation beams emitted by a radiation source (e.g., the radiation source 112). In some embodiments, the filter with a proper thickness may reduce or eliminate radiation beams with specific wavelengths. Exemplary materials of the filter may include aluminum, copper, or the like, or any combination thereof. In some embodiments, the processing device 140 may determine the energy mode by selecting or setting the tube voltage, the target, the filter, or the like, or any combination thereof. For example, the processing device 140 may determine the high energy mode by using a relatively high energy (e.g., 28 KV, 29 KV, 30 KV, etc.). As another example, the processing device 140 may determine the low energy mode by using a relatively low energy (e.g., 22 KV, 24 KV, 26 KV, etc.). In some embodiments, the energy mode may be predetermined and information regarding the energy mode (e.g., setting parameters regarding the tube voltage, the target, the filter, etc.) may be stored in a storage device (e.g., the storage device 150, the storage device 220 of the computing device 200, the storage 390, or an external storage device), and the processing device 140 may access the information regarding the energy mode from the storage device and set the parameters according to the information to implement the energy mode.

As used herein, the contrast agent may be used to enhance the contrast of structures or fluids within the object in an image. An exemplary contrast may include iodine-based compounds, barium-sulfate compounds, etc. In some embodiments, the object may be injected with the contrast agent before being scanned.

In some embodiments, the processing device 140 may direct the plurality of point radiation sources to emit radiation beams according to different manners. For example, the processing device 140 may direct each of the plurality of point radiation sources to emit radiation beams to the ROI to obtain scan data corresponding to the each point radiation source. As another example, the plurality of point radiation sources may include one or more groups of point radiation sources, the processing device 140 may direct each group of point radiation sources to synchronously emit radiation beams. The processing device 140 may direct the groups of point radiation sources to emit radiation beams one group after another in the first mode and direct each group of point radiation sources to synchronously emit radiation beams in the first mode. The radiation of the one or more groups of point radiation sources may be found elsewhere in the present disclosure. See, e.g., FIG. 6 and relevant descriptions thereof.

The first set of data refer to data generated during or after the plurality of point radiation sources emitting radiation beams to the ROI in the first mode. The first set of data may include projection data, one or more image slices, one or more 2D images of the subject, one or more 3D images, one or more 4D images of the object, etc. In some embodiments, the processing device 140 may obtain the first set of data by collecting data corresponding to the plurality of point radiation sources that emit radiation beams to the ROI in the first mode.

For illustration purposes, as shown in FIG. 8, the plurality of point radiation sources may be divided into three groups including a group $B_1$, a group $B_2$, and a group $B_3$. The group $B_1$ may include a point radiation source 811 and a point radiation source 813, the group $B_2$ may include radiation sources 822, 831, and 833, and the group $B_3$ may include point radiation sources 812, 821, 823, and 832. Radiation regions of point radiation sources in each of the group $B_1$, the group $B_2$, and the group $B_3$ may be not overlapped. The processing device 140 may direct the point radiation sources in each of the group $B_1$, the group $B_2$, and the group $B_3$ to synchronously emit radiation beams in the first mode. During or after the point radiation sources in the group $B_1$, the group $B_2$, and the group $B_3$ sequentially emit radiation beams in the first mode, the processing device 140 may generate the first set of data by collecting data corresponding to the plurality of point radiation sources in the group $B_1$, the group $B_2$, and the group $B_3$, and designate the accumulated data corresponding to the plurality of point radiation sources as the first set of data.

In some embodiments, the processing device 140 may obtain the first set of data from one or more other components (e.g., the detector 116 of the imaging device 110, the storage device 150, etc.) of the imaging system 100.

In 1020, the processing device 140 (e.g., the radiation control module 430) may direct the plurality of point radiation sources to emit radiation beams to the ROI in a second mode to generate a second set of data.

In some embodiments, the second mode may include a high energy mode, a low energy mode, a mode in which the object is injected with a contrast agent, a mode in which the object is not injected with the contrast agent, or the like, or any combination thereof. In some embodiments, the second mode may be different from the first mode. For example, the first mode may be the high energy mode, and the second mode may be the low energy mode. As another example, the first mode may be the high energy mode and the mode in which the object is injected with the contrast agent, and the second mode may be the low energy mode and the mode in which the object is injected with the contrast agent. As another example, the first mode may be the mode in which the object is injected with the contrast agent, and the second mode may be the mode in which the object is not injected with the contrast agent. The second set of data refer to scan data generated during or after the plurality of point radiation sources emitting radiation beams to the ROI in the second mode. The second set of data may include projection data, one or more image slices, one or more 2D images of the subject, one or more 3D images, one or more 4D images of the object, etc., which is the same as or similar to the first set of data. The generation of the second set of data may be similar to that of the first set of the data. Merely by way of example, the processing device 140 may direct the point radiation sources in each of the group $B_1$, the group $B_2$, and the group $B_3$ to synchronously emit radiation beams in the second mode. During or after the point radiation sources in the group $B_1$, the group $B_2$, and the group $B_3$ sequentially emit the radiation beams in the second mode, the processing device 140 may generate the second set of data by collecting data corresponding to the plurality of point radiation sources in the group $B_1$, the group $B_2$, and the group $B_3$, and designate the accumulated data corresponding to the plurality of point radiation sources as the second set of data.

In 1030, the processing device 140 (e.g., the obtaining module 410) may obtain scan data relating to the ROI based on the first set of data and the second set of data.

In some embodiments, the scan data relating to the ROI may include projection data, one or more image slices, one or more 2D images of the subject, one or more 3D images, one or more 4D images of the object, etc. Merely by way of example, the scan data may include 3D image data.

In some embodiments, the processing device 140 may obtain the scan data relating to the ROI by processing the first set of data and the second set of data. For example, the processing device 140 may determine a first portion of scan data by combing the first set of data. The first portion of scan data refers to data relating to the ROI corresponding to the first mode. As another example, the processing device 140 may determine a second portion of scan data by combing the second set of data. The second portion of the scan data refers to data relating to the ROI corresponding to the second mode. In some embodiments, the processing device 140 may generate the first portion of scan data and the second portion of scan data using various techniques. In the following descriptions, the determination of the first portion of scan data is taken as an example. The processing device 140 may direct the one or more groups of point radiation sources to emit radiation beams to the ROI in the first mode. Radiation regions of point radiation sources in each group of point radiation sources may have no overlapping region, while radiation regions of two or more point radiation sources in different groups may have overlapping region(s). The processing device 140 may obtain data associated with the overlapping region(s) (e.g., by determining an intersection of the data associated with the overlapping region(s)) and generate one or more image slices.

In some embodiments, the processing device 140 may generate the first portion of scan data by performing e.g., an image reconstruction on the first set of data using an image reconstruction technique. Exemplary algorithms may include an iterative reconstruction algorithm (e.g., a statistical reconstruction algorithm), a Fourier slice theorem algorithm, a fan-beam reconstruction algorithm, an analytic reconstruction algorithm (e.g., a filtered back projection (FBP) algorithm), an algebraic reconstruction technique (ART), a simultaneous algebra reconstruction technique (SART), a Feldkamp-Davis-Kress (FDK) reconstruction technique, or the like, or any combination thereof. The determination of the second portion of the scan data based on the second set of data may be the same as or similar to the determination of the first portion of the scan data based on the first set of data.

In some embodiments, the processing device 140 may obtain the scan data relating to the ROI by performing a fusion operation on the first portion of the scan data and the second portion of the scan data. A fusion operation performed on data refers to a process for gathering multiple data to generate new data which may be relatively consistent, accurate, and useful than the multiple data. The fusion operation of the first set of data and the second set of data may be performed base on various techniques, such as an Nearest neighbor (NN) technique, a K-Means technique, a probabilistic data association (PDA) technique, a joint probabilistic data association (JPDA) technique, a multiple hypothesis test (MHT) technique, a joint probabilistic data association (JPDA-D) technique, a graphical model technique, a state estimation technique, a decision fusion technique, or the like, or any combination thereof.

In some embodiments, the processing device 140 may assign a weight to each of the first portion of the scan data and the second portion of the scan data, and obtain the scan data by fusing the first portion of the scan data and the second portion of the scan data based on the weight thereof (e.g., a weighted sum of the first portion of the scan data and the second portion of the scan data).

In some embodiments, if the first mode is the mode in which the object is injected with the contrast agent, and the second mode is the mode in which the object is not injected with the contrast agent, then the scan data may include data associated with the contrast agent. For example, the processing device 140 may obtain the scan data associated with the contrast agent by subtracting a log-weighted result of the first portion of the scan data and a log-weighted result of the second portion of the scan data. In some embodiments, different regions of the object may have different absorption for the contrast agent (e.g., a tumor region may have relatively large absorption for the contrast agent), then the scan data associated with the contrast agent may be used to generate the target image in which the tumor region may be clearly represented, thereby improving the efficiency and accuracy for detecting some regions (e.g., the tumor region) of the object.

In 1040, the processing device 140 (e.g., the image generation module 440) may generate a target image of the ROI based on the scan data.

In some embodiments, the processing device 140 may generate a first image and a second image based on the first portion of the scan data and the second portion of the scan data, respectively, using the aforementioned image reconstruction technique. In some embodiments, the first image may be an image of the ROI, and information (e.g., a gray value, a contrast, etc.) associated with a portion of the ROI may be enhanced in the first image. In some embodiments, the second image may be an image of the ROI, and information (e.g., a gray value, a contrast, etc.) associated with another portion of the ROI may be enhanced in the second image. For example, if the first mode is the high energy mode, the information associated with a portion (e.g., the bone) of the ROI with a relatively large density may be enhanced in the first image; if the second mode is the low energy mode, the information associated with another portion (e.g., a gray value, a contrast, etc.) of the ROI with a relatively small density may be enhanced in the second image. As another example, if the first mode is a mode in which the object is injected with the contrast agent, a portion (e.g., a cancer region, etc.) of the ROI, which may have a relatively large absorption for the contrast agent, may be enhanced. In this case, information associated with one or more portions of the ROI may be enhanced in the image (e.g., the first image, the second image, etc.), thereby reducing or avoiding misdiagnosis for the ROI, improving the recognizing efficiency of the ROI, and further improving the accuracy of the diagnosis or treatment of a patient including the ROI. In some embodiments, a type of the second image may be the same as or similar to the first image. For example, the first image and the second may be CT images.

The processing device 140 may generate the target image based on the first image and the second image. For example, the processing device 140 may generate the target image by performing a fusion operation on the first image and the second image. A fusion operation performed on images refers to a process configured to gather information of at least two images to generate a fused image. In some embodiments, the processing device 140 may fuse the first image and the second image using, for example, an optimal seamline algorithm, a gradient pyramid algorithm, etc.

A resolution of the target image of the ROI generated by fusing the first image and the second of the ROI may be improved. For illustration purposes, if the ROI includes a first sub-region and a second sub-region, the first sub-region may have a relatively large density, and the second sub-region may have a relatively low density. If the first image is generated in the high energy mode and the second image is generated in the low energy mode, the first image and the second image may include morphological information (e.g., a contour, an edge, etc.) of the ROI, a resolution of the first sub-region in the first image may be larger than a resolution of the first sub-region in the second image, and the resolution of the second sub-region in the second image may be larger than the resolution of the second sub-region in the first image. In this case, in the target image generated by fusing the first image and the second image, the resolution of the first sub-region and the resolution of the second sub-region may be both improved, accordingly, the resolution of the ROI may be improved, and the ROI can be effectively recognized for further diagnosis or treatment.

In some embodiments, the processing device 140 may directly generate the target image based on the scan data obtained by fusing the first portion of the scan data and the second portion of the scan data, for example, using the aforementioned image reconstruction technique(s).

It should be noted that the above description regarding the process 1000 is merely provided for the purposes of illustration, and not intended to limit the scope of the present disclosure. For persons having ordinary skills in the art, multiple variations and modifications may be made under the teachings of the present disclosure. In some embodiments, the first set of data and the second set of data may be obtained at different time points. For example, the first set of data may be obtained before a puncture device is inserted into an object, and the second set of data may be obtained during or after the puncture device is inserted into the object (e.g., the blood vessel of the object). The scan data obtained according to process 1000 may relate to the blood vessel and the puncture device.

The descriptions of the generation of the first set of data and/or the second set of data are merely provided for the purposes of illustration, and not intended to limit the scope of the present disclosure. For example, the processing device 140 may sequentially direct each of the plurality of point radiation sources to emit radiation beams to the ROI in the first mode and the second mode, respectively, and data corresponding to the plurality of point radiation sources in the first mode may be collected as the first set of data, data corresponding to the plurality of point radiation sources in the second mode may be collected as the second set of data. As another example, the processing device 140 may synchronously direct the plurality of point radiation sources to emit radiation beams in the first mode (or the second mode) to generate the first set of data (or the second set of data). As yet another example, the processing device 140 may direct the plurality of point radiation sources to emit radiation beams in the first mode and the second mode one after one.

However, those variations and modifications do not depart from the scope of the present disclosure. The operations of the illustrated process 1000 are intended to be illustrative. In some embodiments, the process 1000 may be accomplished with one or more additional operations not described, and/or without one or more of the operations discussed.

Figure 11:
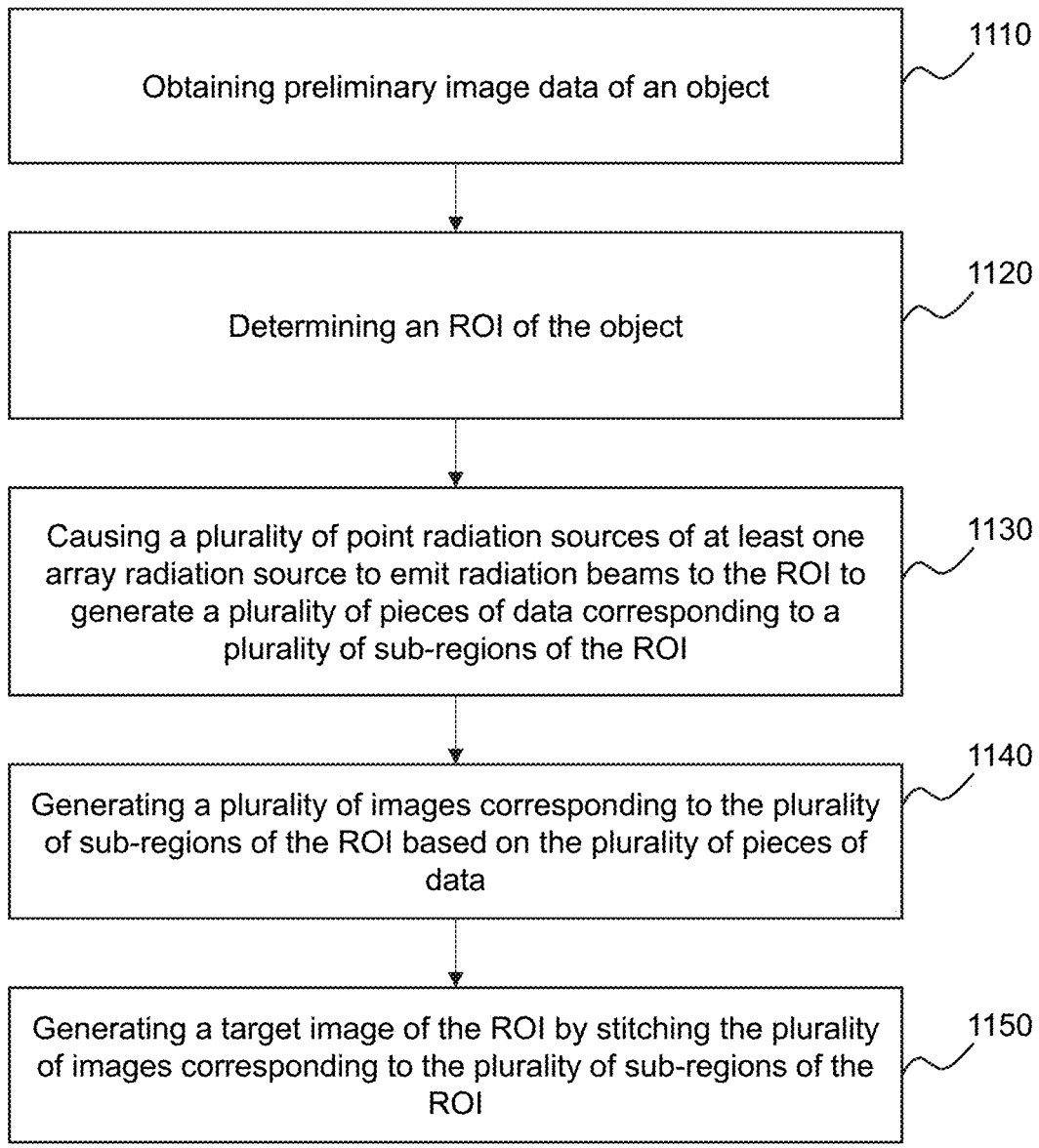
FIG. 11 is a flowchart illustrating an exemplary process for generating a target image of an ROI according to some embodiments of the present disclosure.

FIG. 11 is a flowchart illustrating an exemplary process for generating a target image of an ROI according to some embodiments of the present disclosure. In some embodiments, the process 1100 may be an exemplary embodiment of operation 560 as described in connection with FIG. 5. In some embodiments, one or more operations of process 1100 illustrated in FIG. 11 may be implemented in the imaging system 100 illustrated in FIG. 1. For example, the process 1100 may be stored in a storage device (e.g., the storage device 150, the storage device 220, or the storage 390) of the imaging system 100 in the form of instructions, and invoked and/or executed by the processing device 140 (e.g., the processor 210 of the computing device 200 as illustrated in FIG. 2, the CPU 340 of the mobile device 300 as illustrated in FIG. 3, or one or more modules of the processing device 140 illustrated in FIG. 4).

In 1110, the processing device 140 (e.g., the obtaining module 410) may obtain preliminary image data of an object.

In some embodiments, the preliminary image data may include image data (e.g., scan data, projection data) and/or images of various forms, including a two-dimensional (2D) image, a three-dimensional (3D) image, a four-dimensional (4D), one or more image slices, etc. The obtaining of the preliminary image data may be the same as or similar to the obtaining of the preliminary image described in operation 510 in FIG. 5.

In 1120, the processing device 140 (e.g., the ROI determination module 450) may determine an ROI of the object.

In some embodiments, the processing device 140 may determine the ROI of the object. More descriptions of the determination of the ROI may be found elsewhere in the present disclosure (e.g., FIG. 5 and descriptions thereof).

In 1130, the processing device 140 (e.g., the radiation control module 430) may cause the plurality of point radiation sources of the at least one array radiation source to emit radiation beams to the ROI to generate a plurality of pieces of data corresponding to a plurality of sub-regions of the ROI.

In some embodiments, at least one array radiation source may be used to emit radiation beams to the ROI of the object. The at least one array radiation source may include a plurality of point radiation sources. Each of the plurality of point radiation sources may have a radiation region on a detector (e.g., the detector 116). The ROI may include a plurality of sub-regions. A union set of the plurality of sub-regions may form the ROI. In some embodiments, two or more of the plurality of sub-regions may have an overlapping region. In some embodiments, at least one sub-region (e.g., each sub-region) may overlap with radiation regions of two or more point radiation sources of the plurality of point radiation sources. In some embodiments, at least one sub-region (e.g., each sub-region) may be covered by or may overlap with an overlapping region (or an intersection) of radiation regions of two or more point radiation sources.

Figure 13:
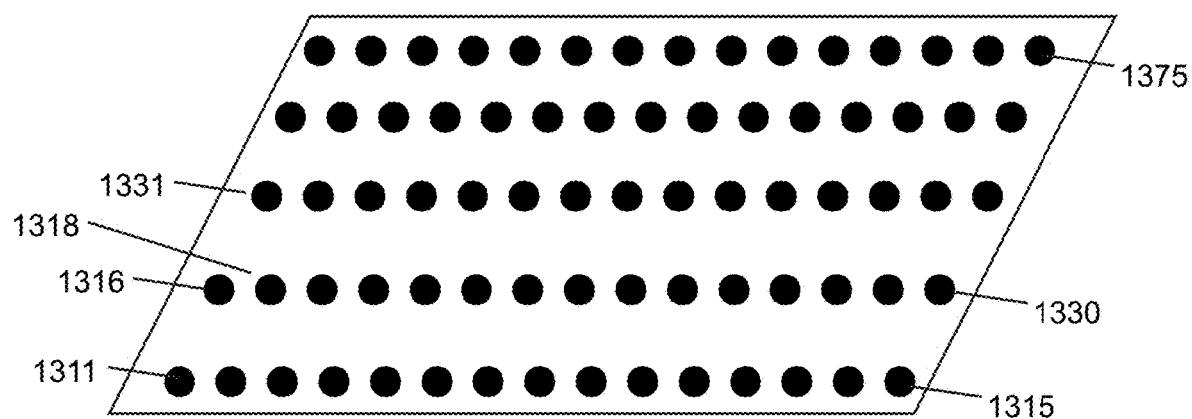
FIG. 13 is a schematic diagram illustrating an exemplary array radiation source according to some embodiments of the present disclosure.
Figure 14:
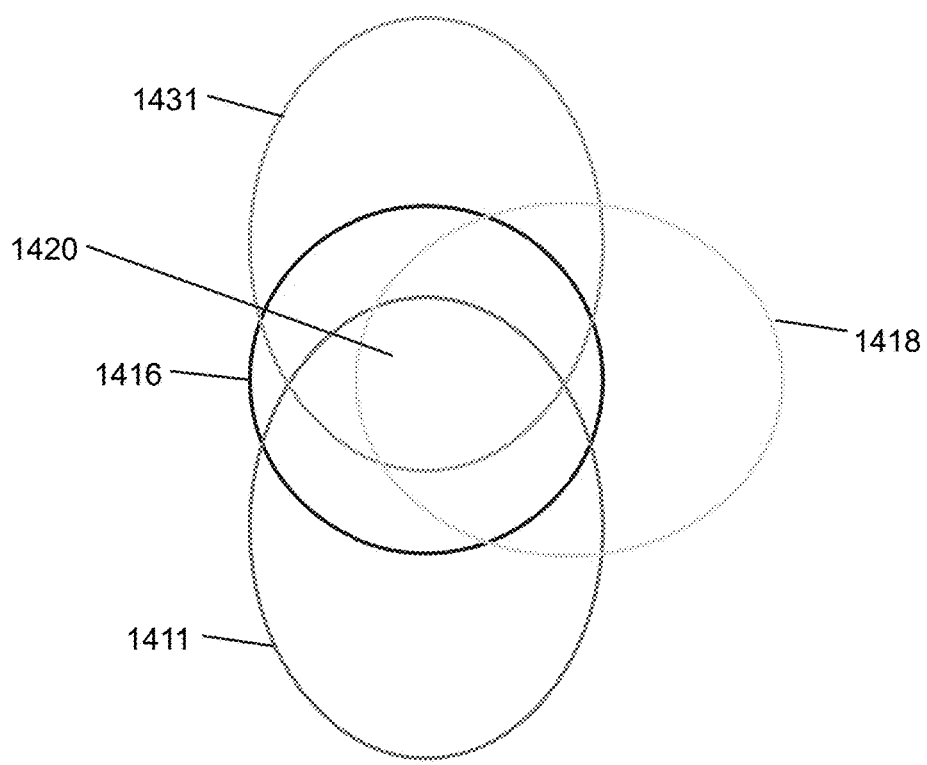
FIG. 14 is a schematic diagram illustrating radiation regions of one or more point radiation sources in the array radiation source in FIG. 13.

In some embodiments, the at least one array radiation source may include a first array radiation source having a planar arrangement and a second array radiation source having a linear arrangement. The processing device 140 may determine one or more first sub-regions of the ROI corresponding to the first array radiation source (e.g., by determining intersection(s) of first radiation regions of point radiation sources of the first array radiation source). The processing device 140 may determine one or more second sub-regions of the ROI corresponding to the second array radiation source (e.g., by determining intersection(s) of second radiation regions of point radiation sources of the second array radiation source). The processing device 140 may determine the one or more sub-regions of the ROI by combining the one or more first sub-regions and the one or more second sub-regions. For example, a union set of the one or more first sub-regions and the one or more second sub-regions may form the one or more sub-regions of the ROI. For illustration purposes, the determination of the first sub-region(s) is described as an example. The processing device 140 may determine the first sub-region(s) based on the overlapping region(s) (or intersection(s)) of radiation regions of the point radiation sources in the first array radiation source. Specifically, the processing device 140 may obtain position information associated with each of the radiation regions of the point radiation sources in the first array radiation source. The position information may be determined based on one or more parameters associated with each point radiation source in the first array radiation source. The one or more parameters may include an SID, an SOD, a cone angle of radiation beams of the each point radiation source, a size of a detector, a pixel size of the detector, a position of the each point radiation source, or the like, or any combination thereof. In some embodiments, the position information of each of the radiation regions may be represented by a coordinate in a coordinate system (e.g., the coordinate system 160). The processing device 140 may determine the one or more sub-regions of the ROI based on the position information associated with each of the radiation regions. The position information associated with each of the radiation regions may be determined based on one or more parameters associated with each point radiation source of the two or more point radiation sources. Specifically, the processing device 140 may determine intersections of the radiation regions to determine the one or more sub-regions of the ROI. For illustration purposes, FIG. 13 is a schematic diagram illustrating an exemplary array radiation source 1300 according to some embodiments of the present disclosure. As shown in FIG. 13, the array radiation source 1300 may include seventy-five point radiation sources (e.g., point radiation source 1311, ..., 1315, 1316, ..., 1330, 1331, ..., 1375). In some embodiments, the array radiation source 1300 may include a plurality of groups of point radiation sources. Radiation regions of each group of point radiation sources may have no overlapping region. Radiation regions of two or more point radiation sources in different groups may have overlapping regions. FIG. 14 is a schematic diagram illustrating radiation regions of one or more point radiation sources in the array radiation source 1300 in FIG. 13. In some embodiments, the radiation regions in FIG. 14 may be formed when the point radiation sources in FIG. 13 emit radiation beams to a detector. More descriptions regarding the radiation manners of the point radiation sources may be found elsewhere in the present disclosure. See, e.g., operation 540 in FIG. 5 and the relevant descriptions thereof. As shown in FIG. 14, a radiation region 1411 corresponds to the point radiation source 1311, a radiation region 1416 corresponds to the point radiation source 1316, a radiation region 1431 corresponds to the point radiation source 1331, and a radiation region 1418 corresponds to the point radiation source 1318. In some embodiments, the point radiation source 1311, the point radiation source 1316, the point radiation source 1331, and the point radiation source 1318 may be in different groups of the plurality of groups of point radiation sources. The radiation regions 1411, 1416, 1431, and 1418 may have an overlapping region or have an intersection (e.g., an overlapping region 1420), which may correspond to a sub-region of the ROI.

Figure 15:
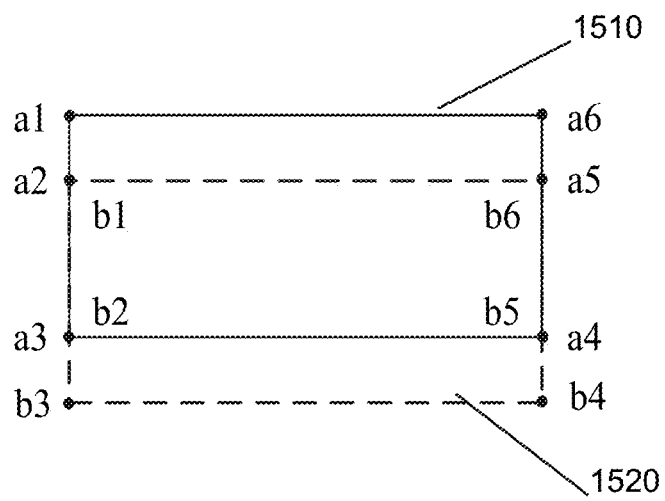
FIG. 15 is a schematic diagram illustrating an exemplary sub-region according to some embodiments of the present disclosure.

In some embodiments, the processing device 140 may determine the plurality of sub-regions of the ROI of the object based on one or more edge points corresponding to intersections of the radiation regions of the plurality of point radiation source. For example, the processing device 140 may determine an intersection of two or more adjacent radiation regions of at least two point radiation sources. Specifically, the processing device 140 may determine first edge points corresponding to the adjacent radiation regions based on the intersection. An edge point refers to a point on a boundary of a region. The processing device 140 may determine a plurality of third edge points of each of overlapping radiation regions using an edge point extraction algorithm. The processing device 140 may determine whether at least one edge point in the plurality of third edge points of one radiation region of the adjacent radiation regions is the same as that of another radiation region of the adjacent radiation regions. In response to the determination that the at least one edge point in the plurality of third edge points of one radiation region of the adjacent radiation regions is the same as that of another radiation region of the adjacent radiation regions, the at least one edge point may be regarded as the first edge point. For illustration purposes, FIG. 15 is a schematic diagram illustrating an exemplary sub-region according to some embodiments of the present disclosure. As shown in FIG. 15, 1510 refers to a radiation region of a point radiation source of two adjacent point radiation sources (e.g., the first point radiation sources or the second point radiation sources) indicated by a solid bounding box, and 1520 refers to another radiation region of another point radiation source of the two adjacent point radiation sources indicated by a dotted bounding box. A boundary of the radiation region 1510 includes six third edge points (i.e., third edge points a1, a2, a3, a4, a5, and a6), and coordinates of the six third edge points on the boundary of the radiation region 1510 in the coordinate system are respectively (1, 15), (1, 12), (1, 6), (20, 6), (20, 12), and (20, 15). The boundary of the radiation region 1320 includes six third edge points (i.e., third edge points b1, b2, b3, b4, b5, and b6), and coordinates of the six third edge point on the boundary of the radiation region 1520 in the coordinate system are (1, 12), (1, 6), (1, 3), (20, 3), (20, 6), and (20, 12). The coordinate of the third edge point a2 is the same as that of the third edge point b1, and the coordinate of the third edge point a3 is the same as that of the third edge point b2, the coordinate of the third edge point a4 is the same as that of the third edge point b5, and the coordinate of the third edge point a5 is the same as that of the third edge point b6. The processing device 140 may designate the third edge point a2 (i.e., the third point b1), the third edge point a3 (i.e., the third point b2), the third edge point a4 (i.e., the third point b5), and the third edge point a5 (i.e., the third point b6) as the first edge points.

The processing device 140 may determine the first sub-regions based on the plurality of first edge points. For example, the processing device 140 may designate area(s) enclosed by the plurality of first edge points as the first sub-region(s). As another example, the processing device 140 may determine the first sub-regions by fitting the plurality of first edge points using a curve fitting technique, a linear fitting technique, or other fitting techniques.

The determination of the second sub-regions may be the same as or similar to the determination of the first sub-regions described aforementioned and is not repeated herein. The accuracy of the sub-regions determined using the aforementioned method may be improved, and the accuracy of a plurality of images corresponding to the plurality of sub-regions of the ROI generated based on the plurality of pieces of data may be improved.

A piece of data refers to scan data corresponding to a sub-region of the plurality of sub-regions of the ROI when the processing device 140 causes the plurality of point radiation sources to emit radiation beams to the ROI. In some embodiments, radiation regions of two or more point radiation sources of the plurality of point radiation sources may cover a specific sub-region of the ROI. In some embodiments, a piece of data corresponding to a sub-region may refer to scan data generated based on radiation beams emitted by the point radiation sources that have radiation regions cover the sub-region. For example, as shown in FIG. 13 and FIG. 14, the sub-region 1420 may be covered by the radiation regions of the point radiation source 1311, point radiation source 1316, point radiation source 1318, and point radiation source 1331. The piece of data may include the scan data generated based on radiation beams emitted by the point radiation source 1311, point radiation source 1316, point radiation source 1318, and point radiation source 1331.

In some embodiments, the piece of data may be generated by fusing the scan data generated based on radiation beams emitted by the two or more point radiation sources. For example, as shown in FIG. 13 and FIG. 14, the piece of data corresponding to the sub-region 1420 may be generated by fusing the scan data generated based on radiation beams emitted by the point radiation sources 1311, 1316, 1318, and 1331 associated with the sub-region 1420.

In some embodiments, each of the plurality of pieces of data may correspond to a plurality of image slices or may include PET data (e.g., gamma photon information), SPECT data (e.g., gamma photon information), CT data (e.g., projection data), or the like, or any combination thereof. In some embodiments, the processing device 140 may obtain the plurality of pieces of data from one or more components (e.g., the detector 116 of the imaging device 110, the storage device 150) of the imaging system 100. In some embodiments, the plurality of pieces of data may be 2D scan data, 3D scan data, 4D scan data, or the like, or any combination thereof. More descriptions regarding the radiation of the plurality of point radiation sources may be found elsewhere in the present disclosure. See, e.g., FIG. 6 and FIG. 10, and the relevant descriptions thereof.

In 1140, the processing device 140 (e.g., the image generation module 440) may generate a plurality of images corresponding to the plurality of sub-regions of the ROI based on the plurality of pieces of data.

In some embodiments, if a piece of data (e.g., a 3D image block) is generated by fusing scan data of the two or more point radiation sources, the piece of data may correspond to a sub-region of the plurality of sub-regions. The plurality of images may be generated based on the plurality of pieces of data. In some embodiments, the processing device 140 may generate the plurality of images corresponding to the plurality of sub-regions of the ROI using an image reconstruction technique as described in FIG. 10.

In some embodiments, each of the pieces of data may correspond to a plurality of slice images. For example, the processing device 140 may determine a slice image based on scan data corresponding to each of the plurality of point radiation sources. The processing device 140 may determine a piece of data (corresponding to a 3D image block) by reconstructing the plurality of image slices, e.g., using the image reconstruction technique as described in FIG. 10. For example, for the sub-region 1420 in FIG. 14, slice images may be generated based on scan data generated based on radiation beams emitted by the point radiation source 1311, point radiation source 1316, point radiation source 1318, and point radiation source 1331, respectively. In some embodiments, the processing device 140 may determine slice information relating to the plurality of image slices. The slice information may include a layer number of each of the image slices, a layer thickness of each of the image slices, a stitching sequence of the image slices, or the like, or any combination thereof. The layer thickness of each of the image slices may be denoted by a reconstruction interval. The number (or the count) of the image slices in different pieces of data may be the same or different.

In 1150, the processing device 140 (e.g., the image generation module 440) may generate a target image of the ROI by stitching the plurality of images corresponding to the plurality of sub-regions of the ROI.

In some embodiments, the processing device 140 may determine a relative position relationship between the plurality of sub-regions of the ROI in the plurality of images. In some embodiments, position information associated with the plurality of sub-regions may be determined based on the position information associated with each of the radiation regions. A relative position relationship between the plurality of sub-regions may be determined based on the position information associated with the plurality of sub-regions. The processing device 140 may stitch the plurality of sub-regions to generate the target image based on the relative position relationship between the plurality of sub-regions For example, the processing device 140 may stitch the plurality of sub-regions from one or more sub-regions on a left side of the detector to one or more sub-regions on a right side of the detector (as indicated by an arrow A in FIG. 12), from one or more sub-regions on a back side of the detector to one or more sub-regions on a front side of the detector (as indicated by an arrow B in FIG. 12), or according to other orders.

In some embodiments, the stitching of the plurality of images may be performed using a direct technique, a feature-based technique (e.g., a Harris algorithm, a Scale-Invariant Feature Transform (SIFT) algorithm, a Speeded Up Robust Features (SURF) algorithm, a Features from Accelerated Segment Test (FAST) algorithm, a PCA-SIFT algorithm, an ORB algorithm, etc.), or the like, or any combination thereof. When using the direct technique, a plurality of pixels in an image may be compared with a plurality of pixels in another image to determine an overlapping region between two images. When using the feature-based technique, one or more features (e.g., points, lines, edges, corners, or any other shapes) of an image may be compared with one or more features of another image to determine overlapping region(s) between two images.

In some embodiments, the processing device 140 may perform one or more additional operations on the plurality of images to improve the resolution of the target image. The additional operations may include image registration, image reprojection, image calibration, image compositing, image blending, or the like, or any combination thereof.

In some embodiments, each of the plurality of images corresponding to the plurality of sub-regions of the ROI may include the plurality of image slices. In some embodiments, the number of the image slices in each of the plurality of sub-regions may be the same. The processing device 140 may obtain the slice information relating to image slices of the plurality of images, and stitch the image slices of the plurality of images based on the relative position relationship and the slice information. For example, the processing device 140 may stitch the image slices with the same layer number to generate target slices based on the relative position relationship. The processing device 140 may generate the target image based on the plurality of target slices e.g., by stacking the target slices.

It should be noted that the above description regarding the process 1100 is merely provided for the purposes of illustration, and not intended to limit the scope of the present disclosure. For persons having ordinary skills in the art, multiple variations and modifications may be made under the teachings of the present disclosure. For example, the processing device 140 may generate an image corresponding to each radiation region of the plurality of radiation regions, and generate the target image by stitching the plurality of images corresponding to each radiation region. However, those variations and modifications do not depart from the scope of the present disclosure. The operations of the illustrated process 1100 are intended to be illustrative. In some embodiments, the process 1100 may be accomplished with one or more additional operations not described, and/or without one or more of the operations discussed.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A non-transitory computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby, and Groovy, or other programming languages. The program code may execute entirely on the user's computer, partly on the user's computer, as a stand-alone software package, partly on the user's computer and partly on a remote computer, or entirely on the remote computer or server. In the latter scenario, the remote computer may be connected to the user's computer through any type of network, including a local area network (LAN) or a wide area network (WAN), or the connection may be made to an external computer (e.g., through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities, properties, and so forth, used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A method for generating an image implemented on a computing device having at least one processor and at least one storage device, the method comprising:
   obtaining a preliminary image of an object;
   determining, at least partially based on a region of interest (ROI) of the object, a plurality of point radiation sources of at least one array radiation source, including:
      determining, based on the ROI, a plurality of groups of point radiation sources from the at least one array radiation source, wherein the at least one array radiation source comprises a first array radiation source and a second array radiation source, the first array radiation source is located closed to a breast wall of a breast of the object, the second array radiation source is located away from the breast wall of the breast of the object, the first array radiation source is arranged in a line arrangement, the second array radiation source is arranged in a planar arrangement; and wherein
      the first array radiation source is arranged based on a shape of the breast wall; or
      an arrangement density of the point radiation sources in the first array radiation source is greater than an arrangement density of the point radiation sources in the second array radiation source; or
      the point radiation sources in the first array radiation source are tilted or deflected away from the breast wall such that an angle is formed between radiation beams emitted by the first array radiation source and radiation beams emitted by the second array radiation source;
   determining, based on the preliminary image, at least one scanning parameter associated with the plurality of point radiation sources;
   causing the plurality of point radiation sources to emit, based on the at least one scanning parameter, radiation beams to the ROI to generate scan data relating to the ROI, wherein the plurality of groups of point radiation sources are directed to emit radiation beams one group after another, and each group of point radiation sources are directed to synchronously emit radiation beams;
   obtaining scan data relating to the ROI; and generating a target image of the ROI based on the scan data relating to the ROI.

2. The method of claim 1, wherein the determining a plurality of point radiation sources of at least one array radiation source comprises:
determining, from the at least one array radiation source, the plurality of point radiation sources based on at least one first parameter associated with each point radiation source of the at least one array radiation source and at least one second parameter associated with the ROI.

3. The method of claim 2, wherein
the at least one first parameter associated with each point radiation source of the at least one array radiation source includes at least one of a source-to-image distance (SID), a source-to-object distance (SOD), a position of the each point radiation source, or a radiation region of the each point radiation source.

4. The method of claim 2, wherein the at least one second parameter associated with the ROI includes at least one of a thickness of the ROI, an attenuation characteristic of the ROI, a shape of the ROI, a position of the ROI, or a size of the ROI, and the method further comprises:
determining the at least one second parameter associated with the ROI based on the preliminary image.

5. The method of claim 2, wherein the determining at least one scanning parameter associated with the plurality of point radiation sources comprises:
determining the at least one scanning parameter based on the at least one second parameter.

6. The method of claim 1, wherein
radiation regions of the plurality of groups of point radiation sources cover the ROI; and
radiation regions of each group of point radiation sources have no overlapping region, wherein the radiation region of the point radiation source refers to a region on a detector, which is irradiated by radiation beams emitted by the point radiation source.

7. The method of claim 1, wherein the causing the plurality of point radiation sources to emit radiation beams to the ROI comprises:
directing the plurality of point radiation sources to emit radiation beams to the ROI in a first mode to generate a first set of data; and
directing the plurality of point radiation sources to emit radiation beams to the ROI in a second mode to generate a second set of data.

8. The method of claim 7, further comprising:
determining a first portion of the scan data by combining the first set of data; and
determining a second portion of the scan data by combining the second set of data.

9. The method of claim 8, wherein the obtaining scan data relating to the ROI comprises:
obtaining the scan data relating to the ROI by fusing the first portion of the scan data and the second portion of the scan data.

10. The method of claim 8, wherein the generating a target image of the ROI based on the scan data relating to the ROI comprises:
generating a first image based on the first portion of the scan data;
generating a second image based on the second portion of the scan data; and
generating the target image based on the first image and the second image.

11. The method of claim 7, wherein
the first mode includes a mode in which the radiation beams emitted to the ROI have a relatively high energy, and the second mode includes a mode in which the radiation beams emitted to the ROI have a relatively low energy, or
the first mode includes a mode in which the object is injected with a contrast agent, and the second mode includes a mode in which the object is injected with no contrast agent.

12. The method of claim 1, wherein the scan data relating to the ROI includes a plurality of pieces of data corresponding to a plurality of sub-regions of the ROI, and the generating a target image of the ROI based on the scan data relating to the ROI comprises:
generating, based on the plurality of pieces of data corresponding to the plurality of sub-regions of the ROI, a plurality of images corresponding to the plurality of sub-regions of the ROI, each of the plurality of images corresponding to one of the plurality of sub-regions of the ROI; and
generating the target image of the ROI by stitching the plurality of images corresponding to the plurality of sub-regions of the ROI.

13. The method of claim 12, wherein the plurality of sub-regions include at least one sub-region covered by an overlapping region of radiation regions of two or more point radiation sources of the plurality of point radiation sources.

14. The method of claim 12, wherein the generating the target image of the ROI by stitching the plurality of images corresponding to the plurality of sub-regions of the ROI comprises:
determining a relative position relationship between the plurality of sub-regions of the ROI in the plurality of images; and
stitching, based on the relative position relationship, the plurality of images.

15. The method of claim 12, wherein the generating, based on the plurality of pieces of data corresponding to the plurality of sub-regions of the ROI, a plurality of images corresponding to the plurality of sub-regions of the ROI comprises:
obtaining a plurality of first pieces of data corresponding to a plurality of first sub-regions of the ROI covered by an overlapping region of first radiation regions of at least two point radiation sources of the first array radiation source;
obtaining a plurality of second pieces of data corresponding to a plurality of second sub-regions of the ROI covered by an overlapping region of second radiation regions of at least two point radiation sources of the second array radiation source; and
generating, based on the plurality of first pieces of data and the plurality of second pieces of data, the plurality of images corresponding to the plurality of first sub-regions and the plurality of second sub-regions.

16. A system for generating an image, comprising:
at least one storage device storing a set of instructions; and
at least one processor in communication with the storage device, wherein when executing the set of instructions, the at least one processor is configured to cause the system to perform operations including:
obtaining a preliminary image of an object;
determining, at least partially based on a region of interest (ROI) of the object, a plurality of point radiation sources of at least one array radiation source, wherein the at least one array radiation source comprises a first array radiation source and a second array radiation source, the first array radiation source is located closed to a breast wall of a breast of the object, the second array radiation source is located away from the breast wall of the breast of the object, the first array radiation source is arranged in a line arrangement, the second array radiation source is arranged in a planar arrangement; and wherein the first array radiation source is arranged based on a shape of the breast wall; or an arrangement density of the point radiation sources in the first array radiation source is greater than an arrangement density of the point radiation sources in the second array radiation source; or the point radiation sources in the first array radiation source are tilted or deflected away from the breast wall such that an angle is formed between radiation beams emitted by the first array radiation source and radiation beams emitted by the second array radiation source;

determining, based on the ROI, a plurality of groups of point radiation sources from the at least one array radiation source;

causing the plurality of point radiation sources to emit, based on the at least one scanning parameter, radiation beams to the ROI to generate scan data relating to the ROI, wherein the plurality of groups of point radiation sources are directed to emit radiation beams one group after another, and each group of point radiation sources are directed to synchronously emit radiation beams;

obtaining scan data relating to the ROI; and generating a target image of the ROI based on the scan data relating to the ROI.

17. A method for determining a radiation source implemented on a computing device having at least one processor and at least one storage device, the method comprising:

obtaining a preliminary image of an object;

determining, based on the preliminary image, a region of interest (ROI); and determining, based on the ROI, a plurality of groups of point radiation sources from at least one array radiation source, wherein the at least one array radiation source comprises a first array radiation source and a second array radiation source, the first array radiation source is located closed to a breast wall of a breast of the object, the second array radiation source is located away from the breast wall of the breast of the object, the first array radiation source is arranged in a line arrangement, the second array radiation source is arranged in a planar arrangement; and wherein the first array radiation source is arranged based on a shape of the breast wall; or an arrangement density of the point radiation sources in the first array radiation source is greater than an arrangement density of the point radiation sources in the second array radiation source; or the point radiation sources in the first array radiation source are tilted or deflected away from the breast wall such that an angle is formed between radiation beams emitted by the first array radiation source and radiation beams emitted by the second array radiation source, wherein the plurality of groups of point radiation sources are directed to emit radiation beams one group after another, and each group of point radiation sources are directed to synchronously emit radiation beams.

* * * * *